(12) United States Patent
Würthner et al.

(10) Patent No.: US 8,946,376 B2
(45) Date of Patent: Feb. 3, 2015

(54) SEMICONDUCTORS BASED ON DIKETOPYRROLOPYRROLES

(75) Inventors: Frank Würthner, Höchberg (DE); Sabin-Lucian Suraru, Würzburg (DE); Pascal Hayoz, Hofstetten (CH)

(73) Assignee: BASF SE, Ludwigshafen (DE)

( * ) Notice: Subject to any disclaimer, the term of this patent is extended or adjusted under 35 U.S.C. 154(b) by 579 days.

(21) Appl. No.: 13/246,003

(22) Filed: Sep. 27, 2011

(65) Prior Publication Data

US 2012/0074393 A1   Mar. 29, 2012

Related U.S. Application Data

(60) Provisional application No. 61/387,487, filed on Sep. 29, 2010, provisional application No. 61/450,141, filed on Mar. 8, 2011.

(51) Int. Cl.
*C08G 14/10* (2006.01)
*C07D 519/00* (2006.01)
(Continued)

(52) U.S. Cl.
CPC ............ *C07D 519/00* (2013.01); *C07D 487/04* (2013.01); *H01L 51/0072* (2013.01); *Y02E 10/549* (2013.01)
USPC ............. 528/163; 528/216; 528/117; 528/54; 528/94; 528/377; 528/380; 257/40

(58) Field of Classification Search
USPC ............. 528/163, 216, 117, 54, 94, 377, 380; 257/40
See application file for complete search history.

(56) References Cited

U.S. PATENT DOCUMENTS 4,579,949 A  4/1986  Rochat et al.
4,659,775 A  4/1987  Pfenninger et al.
(Continued)

FOREIGN PATENT DOCUMENTS

EP   2 034 537 A2   3/2009
JP   2006-117591    5/2006
(Continued)

OTHER PUBLICATIONS

U.S. Appl. No. 13/256,943, filed Oct. 5, 2011, Hayoz, et al.
(Continued)

*Primary Examiner* — Shane Fang
(74) *Attorney, Agent, or Firm* — Oblon, Spivak, McClelland, Maier & Neustadt, L.L.P.

(57) ABSTRACT

The present invention relates to 1,4-diketopyrrolo[3,4-c]pyrrole (DPP) derivatives of the below formula

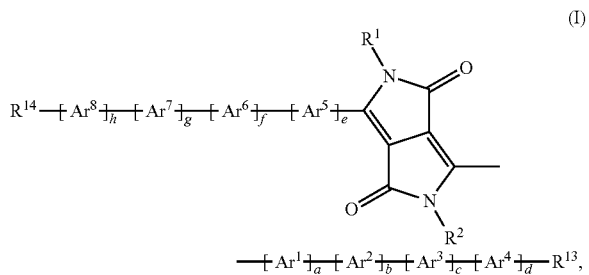

to their manufacture; to their use as organic semiconductors, e.g. in semiconductor devices, especially a sensor, a diode, a photodiode, an organic field effect transistor, a transistor for flexible displays, and/or a solar cell (photovoltaic cell); to such semiconductor devices comprising diketopyrrolopyrrol derivatives of the formula I as a semiconducting effective means, and to devices containing said semiconductor devices. The compounds of the formula I have excellent solubility in organic solvents. High efficiency of energy conversion, excellent field-effect mobility, good on/off current ratios and/or excellent stability can be observed, when said compounds are used in semiconductor devices or organic photovoltaic (PV) devices.

23 Claims, 1 Drawing Sheet

Output and transfer characteristics for bottom-gate top-contact TFT with Cpd. A-1

(51) Int. Cl.
*C07D 487/04* (2006.01)
*H01L 51/00* (2006.01)

(56) References Cited

U.S. PATENT DOCUMENTS

| | | | |
|---|---|---|---|
| 5,703,436 | A | 12/1997 | Forrest et al. |
| 6,420,031 | B1 | 7/2002 | Parthasarathy et al. |
| 6,451,459 | B1 | 9/2002 | Tieke et al. |
| 6,933,436 | B2 | 8/2005 | Shaheen et al. |
| 7,939,818 | B2 | 5/2011 | Heim et al. |
| 2003/0021913 | A1 | 1/2003 | O'Neill et al. |
| 2004/0004433 | A1 | 1/2004 | Lamansky et al. |
| 2006/0013549 | A1 | 1/2006 | Shtein et al. |
| 2007/0079867 | A1 | 4/2007 | Chittibabu et al. |
| 2009/0065766 | A1* | 3/2009 | Li .................... 257/40 |
| 2009/0302311 | A1 | 12/2009 | Turbiez et al. |
| 2010/0032657 | A1 | 2/2010 | Yanai et al. |
| 2011/0004004 | A1 | 1/2011 | Hao et al. |
| 2011/0215313 | A1 | 9/2011 | Düggeli et al. |
| 2011/0240981 | A1 | 10/2011 | Düggeli et al. |

FOREIGN PATENT DOCUMENTS

| | | |
|---|---|---|
| JP | 2007-266285 | 10/2007 |
| JP | 2008-78247 | 4/2008 |
| WO | WO 2004/090046 A1 | 10/2004 |
| WO | WO 2004/112161 A2 | 12/2004 |
| WO | WO 2005/049695 A1 | 6/2005 |
| WO | WO 2008/000664 A1 | 1/2008 |
| WO | WO 2008/001123 A1 | 1/2008 |
| WO | WO 2008/013427 A1 | 1/2008 |
| WO | WO 2009/047104 A2 | 4/2009 |
| WO | WO 2010/049321 A1 | 5/2010 |
| WO | WO 2010/049323 A1 | 5/2010 |
| WO | WO 2010/108873 A1 | 9/2010 |
| WO | WO 2010/115767 A1 | 10/2010 |
| WO | WO 2010/136352 A1 | 12/2010 |
| WO | WO 2010/136353 A1 | 12/2010 |
| WO | WO 2011/049531 A1 | 4/2011 |

OTHER PUBLICATIONS

U.S. Appl. No. 13/260,002, filed Sep. 23, 2011, Hayoz, et al.
U.S. Appl. No. 13/322,668, filed Nov. 28, 2011, Dueggeli, et al.
U.S. Appl. No. 13/321,889, filed Nov. 22, 2011, Lamatsch, et al.
International Search Report and Written Opinion issued Dec. 7, 2011 in Application No. PCT/EP2011/066763.
Prashant Sonar, et al., "Solution processable low bandgap diketopyrrolopyrrole (DPP) based derivatives: novel acceptors for organic solar cells", J. Mater. Chem., vol. 20, 2010, pp. 3626-3636.
Hiroyuki Yanagisawa, et al., "Organic Field-Effect Transistor Devices Based on Latent Pigments of Unsubstituted Diketopyrrolopyrrole or Quinacridone", Japanese Journal of Applied Physics, vol. 47, No. 6, 2008, pp. 4728-4731.
Mananya Tantiwiwat, et al., "Oligothiophene Derivatives Functionalized with a Diketopyrrolopyrrolo Core for Solution-Processed Field Effect Transistors: Effect of Alkyl Substituents and Thermal Annealing", J. Phys. Chem. C, vol. 112, No. 44, 2008, pp. 17402-17407.
Lukas Bürgi, et al., "High-Mobility Ambipolar Near-Infrared Light-Emitting Polymer Field-Effect Transistors", Adv. Mater., vol. 20, 2008, pp. 2217-2224.
Johan C. Bijleveld, et al., "Poly(diketopyrrolopyrrole-terthiophene) for Ambipolar Logic and Photovoltaics", J. Am. Chem. Soc., vol. 131, 2009, pp. 16616-16617.
Bram P. Karsten, et al., "Diketopyrrolopyrroles as Acceptor Materials in Organic Photovoltaics", Macromol. Rapid Commun., vol. 31, 2010, pp. 1554-1559.
Bright Walker , et al., "Small Molecule Solution-Processed Bulk Heterojunction Solar Cells", Chem. Mater., vol. 23, 2011, pp. 470-482.
Sabin-Lucian Suraru, et al., "Diketopyrrolopyrrole as a p-channel organic semiconductor for high performance OTFTs", Chem. Commun., vol. 47, 2011, pp. 1767-1769.
Hannah Burckstümmer, et al., "Synthesis and Characterization of Optical and Redbox Properties of Bithiophene-Functionalized Diketopyrrolopyrrole Chromophores", The Journal of Organic Chemistry, vol. 76, pp. 2426-2432.
U.S. Appl. No. 14/238,382, filed Feb. 11, 2014, Suraru, et al.

* cited by examiner

Output and transfer characteristics for bottom-gate top-contact TFT with Cpd. A-1
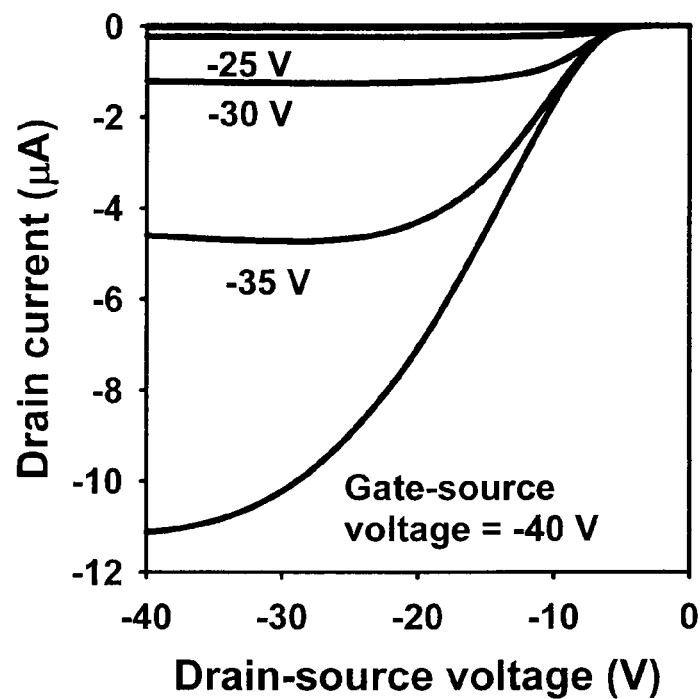
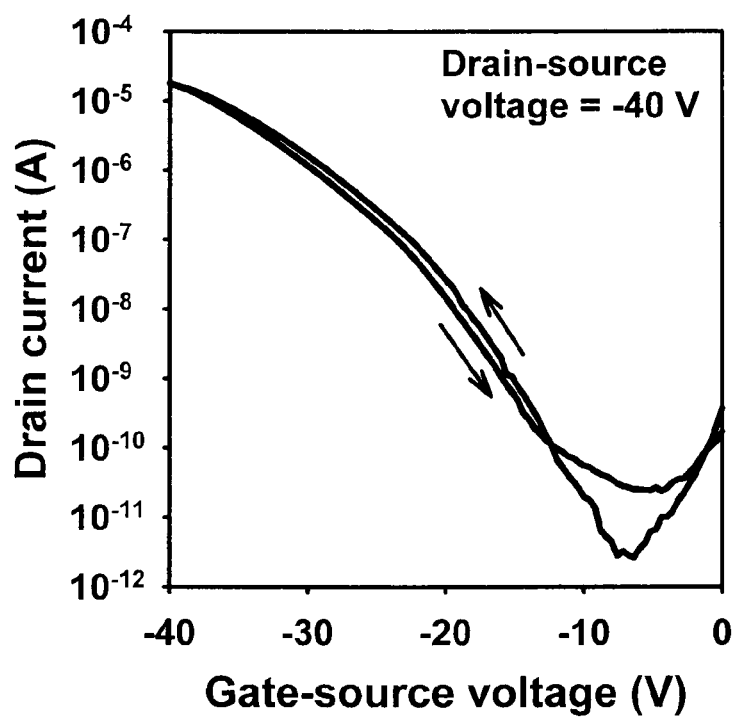

SEMICONDUCTORS BASED ON DIKETOPYRROLOPYRROLES

CROSS REFERENCE TO RELATED APPLICATION

This application claims the benefit of: i) U.S. provisional application No. 61/387,487, filed on Sep. 29, 2010; and ii) U.S. provisional application No. 61/450,141, filed on Mar. 8, 2011.

The present invention relates to 1,4-diketopyrrolo[3,4-c]pyrrole (DPP) derivatives of the below formula I, wherein the substituents are as defined herein below, to their manufacture; to their use as organic semiconductors, e.g. in semiconductor devices, especially a sensor, a diode, a photodiode, an organic field effect transistor, a transistor for flexible displays, and/or a solar cell (photovoltaic cell); to such semiconductor devices comprising diketopyrrolopyrrol derivatives of the formula I as a semiconducting effective means, and to devices containing said semiconductor devices.

Prashant Sonar et al., J. Mater. Chem., 2010, 20, 3626-3636 describes novel low bandgap solution processable diketopyrrolopyrrole (DPP) based derivatives functionalized with electron withdrawing end capping groups (trifluoromethylphenyl and trifluorophenyl):

These compounds showed optical bandgaps ranging from 1.81 to 1.94 eV and intense absorption bands that cover a wide range from 300 to 700 nm, attributed to charge transfer transition between electron rich phenylene-thienylene moieties and the electron withdrawing diketopyrrolopyrrole core. All of the compounds were found to be fluorescent in solution with an emission wavelength ranging from 600 to 800 nm. Bulk heterojunction (BHJ) solar cells using poly(3-hexylthiophene) (P3HT) as the electron donor with these new acceptors were fabricated.

H. Yanagisawa et al., Japan Journal of Applied Physics 47 (2008) 4728-4731 discloses OFETs based on unsubstituted DPP or quinacridone using their solvent soluble precursors called latent pigment. The use of latent pigments enables to fabricate OFETs by spin-coating. A DPP-Pigment with a lactam-NH-group

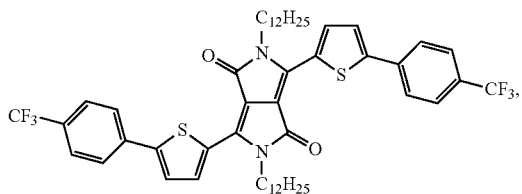

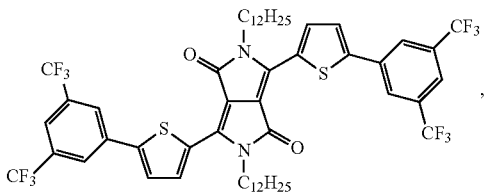

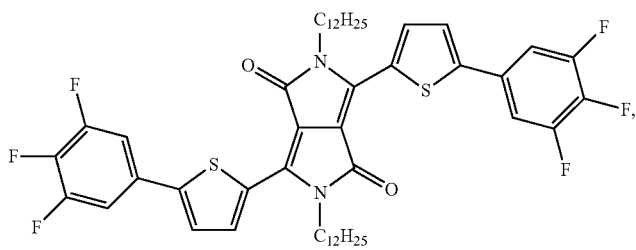

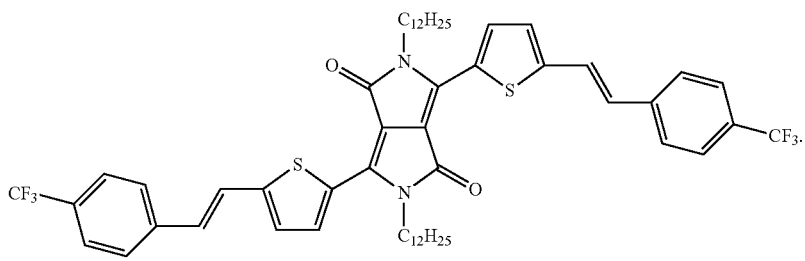

(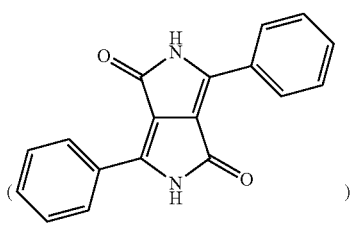 [SMILES: O=C1NC(c2ccccc2)=C2C(=O)NC(c3ccccc3)=C12])

deposited in vacuum was compared to the Boc-protected analogue (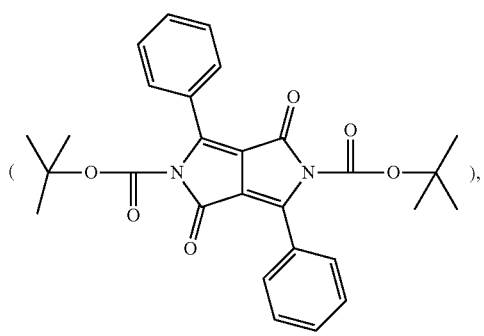 [SMILES: CC(C)(C)OC(=O)N1C(=O)C2=C(c3ccccc3)N(C(=O)OC(C)(C)C)C(=O)C2=C1c1ccccc1]), which was spin-coated from solution and treated afterwards at higher temperature to deprotect the carbamate. Thereby hole-mobilities of ~$10^{-5}$ and ~$10^{-6}$ cm$^2$ V$^{-1}$ s$^{-1}$ were measured respectively.

Thuc-Quyen Nguyen et al., J. Phys. Chem. C 2008, 112, 17402-17407 discloses two new oligothiophene derivatives bearing a diketopyrrolopyrrole core, 2,5-di-n-hexyl-3,6-bis (5-n-hexyl[2,2';5',2"]terthiophen-5-yl)pyrrolo[3,4-c]pyrrole-1,4-dione (DHT6DPPC6) and 2,5-di-n-dodecyl-3,6-bis (5"-n-hexyl[2,2';5',2"]terthiophen-5-yl)pyrrolo[3,4-c] pyrrole-1,4-dione (DHT6DPPC12), and their use in solution-processed organic field effect transistors. The field effect mobilities for annealed DHT6DPPC6 and DHT6DPPC12 films are 0.02 and 0.01 cm$^2$/V s, respectively.

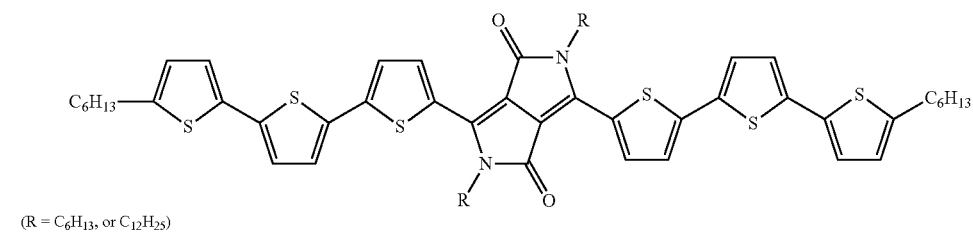

(R = C$_6$H$_{13}$, or C$_{12}$H$_{25}$)

C. Winnewisser et al., Advanced Materials 20 (2008) 2217-2224 discloses a polymer semiconductor,

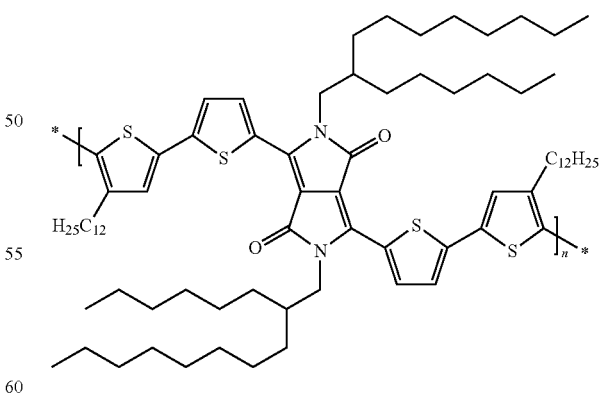

(BBTDPP1), with ambipolar charge transport properties. Ambipolar field-effect transistors based on this material exhibit hole and electron mobilities of 0.1 cm$^2$ V$^{-1}$ s$^{-1}$ and up to 0.09 cm$^2$ V$^{-1}$ s$^{-1}$, respectively.

R. A. J. Janssen et al., J. Am. Chem. Soc. 131 (2009) 16616-16617 report that

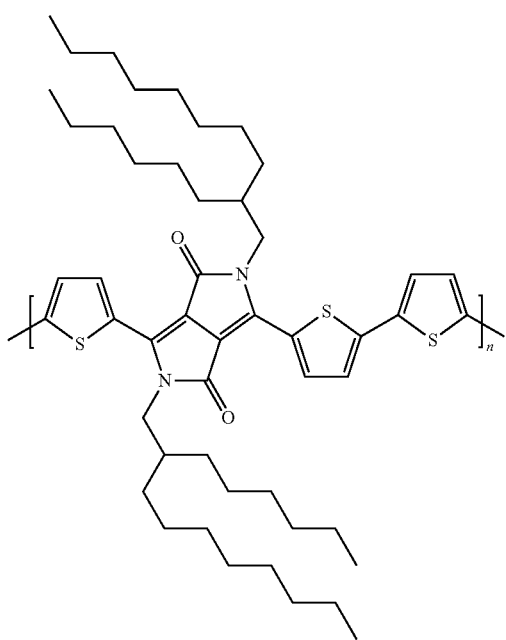

(PDPP3T) exhibits ambipolar transport in FETs with nearly balanced electron and hole mobilities in the $10^{-2}$ cm$^2$ V$^{-1}$ s$^{-1}$ range, making it an interesting candidate for CMOS-like circuits. At a high molecular weight, PDPP3T reaches η=4.7% in photovoltaic cells when combined with [70]PCBM and has a photoresponse up to 900 nm.

R. A. J. Janssen et al., Macromol. Rapid Commun. 31 (2010) 1554-1559 disclose small molecule DPP derivatives

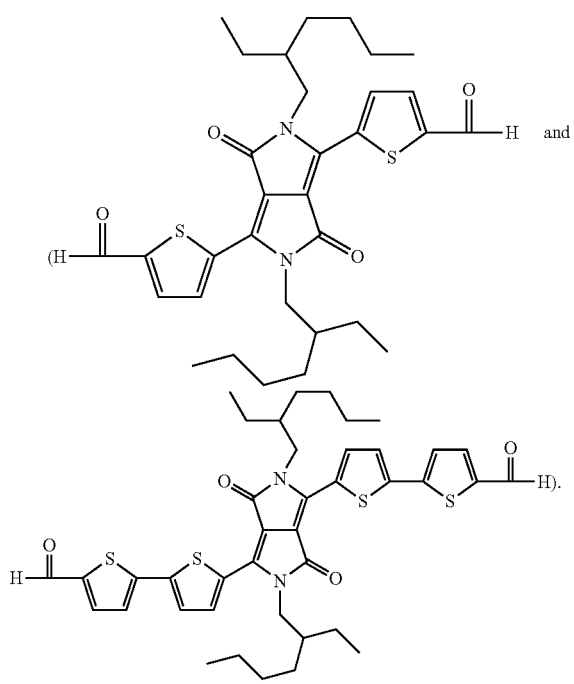

The compounds are tested as electron acceptors in combination with poly(3-hexylthiophene) (P3HT) as the donor material. Working photovoltaic devices are obtained that show a photoresponse in the wavelength region where the DPP molecules absorb. The best device shows a power conversion efficiency of 0.31% in simulated solar light, with a photon-to-electron conversion efficiency of ca. 10% up to 700 nm.

WO2004/090046 relates to fluorescent diketopyrrolopyrroles of the formula I

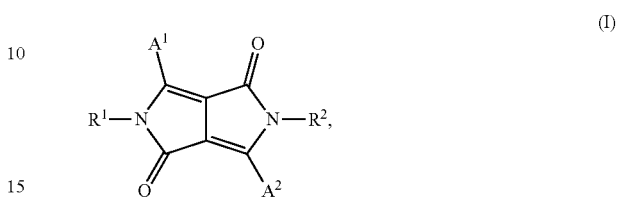

wherein $R^1$ and $R^2$ may be the same or different and are selected from a $C_1$-$C_{25}$alkyl group, which can be substituted by fluorine, chlorine or bromine, an allyl group, which can be substituted one to three times with $C_1$-$C_4$alkyl, a cycloalkyl group, a cycloalkyl group, which can be condensed one or two times by phenyl which can be substituted one to three times with $C_1$-$C_4$-alkyl, halogen, nitro or CN, an alkenyl group, a cycloalkenyl group, an alkynyl group, a haloalkyl group, a haloalkenyl group, a haloalkynyl group, a ketone or aldehyde group, an ester group, a carbamoyl group, a ketone group, a silyl group, a siloxanyl group, $A^3$ or —$CR^3R^4$—$(CH_2)_m$-$A^3$ wherein $R^3$ and $R^4$ independently from each other stand for hydrogen or $C_1$-$C_4$alkyl, or phenyl which can be substituted one to three times with $C_1$-$C_4$alkyl, $A^3$ stands for aryl or heteroaryl, in particular phenyl or 1- or 2-naphthyl which can be substituted one to three times with $C_1$-$C_8$alkyl and/or $C_1$-$C_8$alkoxy, and m stands for 0, 1, 2, 3 or 4, $A^1$ and $A^2$ are independently of each other

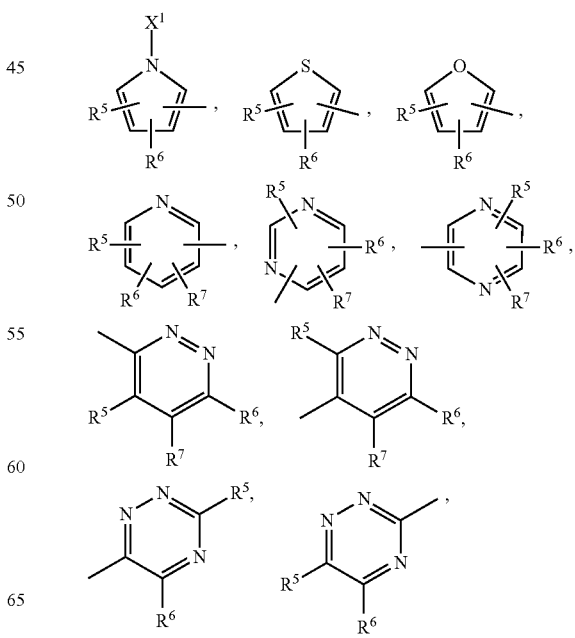

-continued

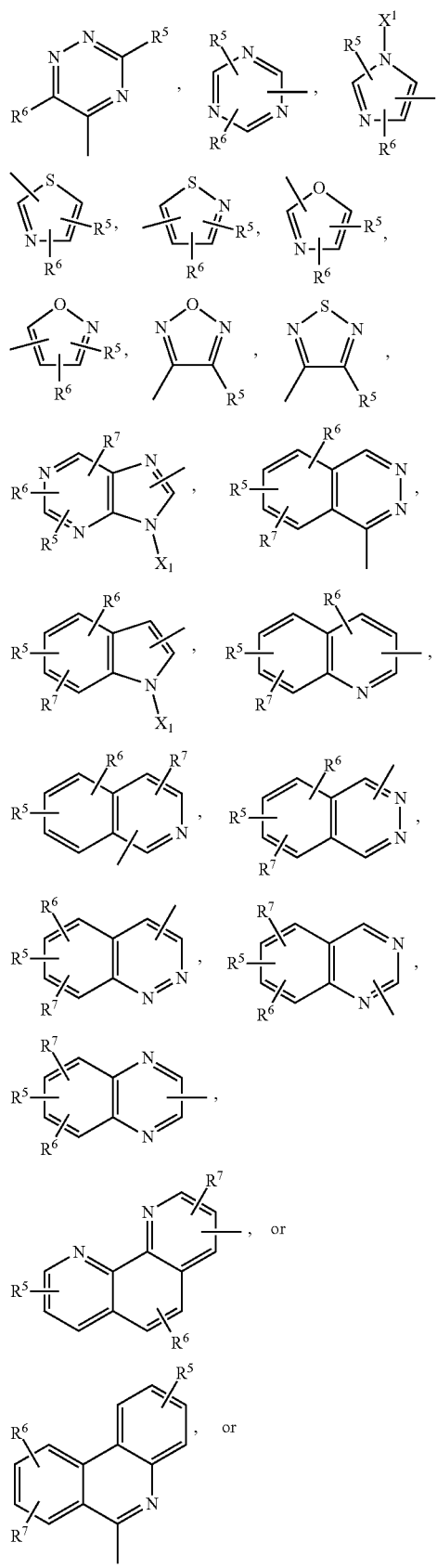

A¹ and A² are independently of each other a group

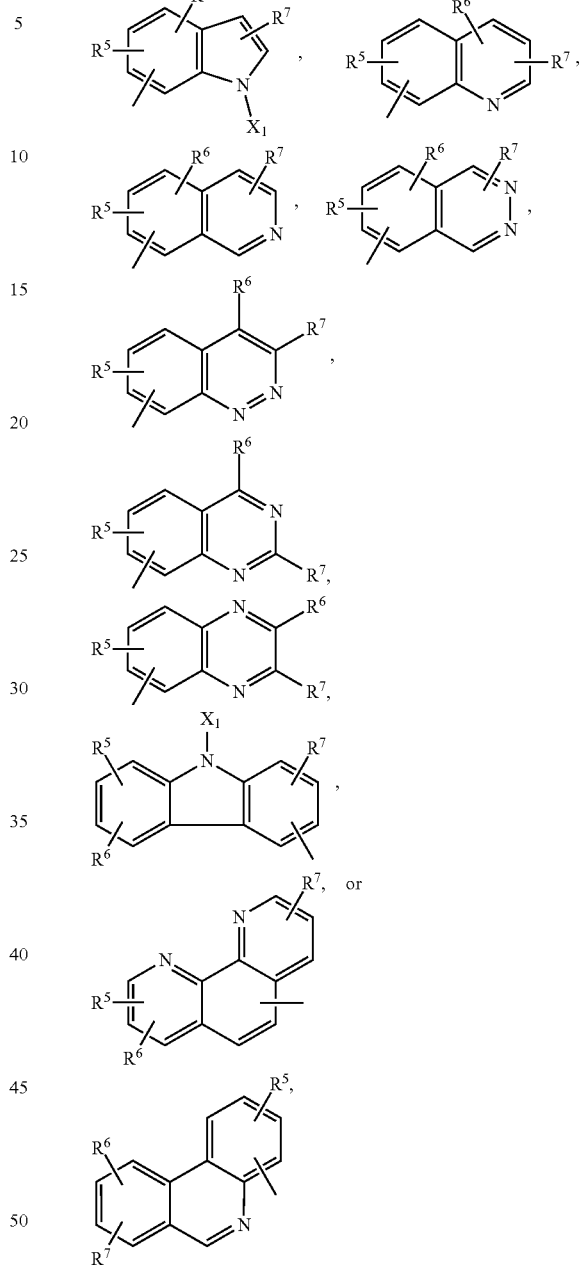

wherein $R^5$, $R^6$, and $R^7$ may be the same or different and are selected from a hydrogen atom, a $C_1$-$C_{25}$alkyl group, a cycloalkyl group, an aralkyl group, an alkenyl group, a cycloalkenyl group, an alkynyl group, a hydroxyl group, a mercapto group, an alkoxy group, an alkylthio group, an aryl ether group, an aryl thioether group, an aryl group, a heterocyclic group, a halogen atom, a haloalkyl group, a haloalkenyl group, a haloalkynyl group, a cyano group, an aldehyde group, a carboxyl group, an ester group, a carbamoyl group, a nitro group, a silyl group, a siloxanyl group, a substituted or unsubstituted vinyl group, a group $NR^8R^9$, wherein $R^8$ and $R^9$ independently of each other stand for a hydrogen atom, an alkyl group, a cycloalkyl group, an aryl group, a heteroaryl group, a heterocyclic group, an aralkyl group, or R⁸ and R⁹ together with the nitrogen atom to which they are bonded form a five or six membered heterocyclic ring, which can be condensed by one or two optionally substituted phenyl groups, or at least two adjacent substituents R⁵ to R⁷ form an aromatic or aliphatic fused ring system, and X¹ is a hydrogen atom, a $C_1$-$C_{25}$ alkyl group, a cycloalkyl group, an aralkyl group, an aryl group, or a heterocyclic group, wherein at least one of the groups R⁵, R⁶, and R⁷ is different from a hydrogen atom, if A¹ and A² are a single five- or six-membered heterocyclic ring, containing one heteroatom selected from the group of nitrogen, oxygen and sulfur.

JP2006117591A relates to compounds of formula

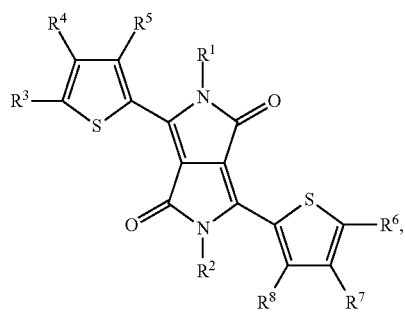

wherein R¹, R²=(un)substituted alkyl group, aryl group or heterocyclic group; R³-R⁸=H, halogen, cyano group, (un)substituted alkyl group, alkoxy group, aryl group, aryloxy group, alkyl thio group, aryl thio group, alkyl carbonyl group, aryl carbonyl group or amino group; X¹, X²=oxygen, sulfur or —NR⁹; and R⁹=H, (un)substituted alkyl, aryl or heterocyclic group, or R¹-R⁹ are combined to form a ring, and their use in organic electroluminescent elements. Among others the following compounds are explicitly mentioned:

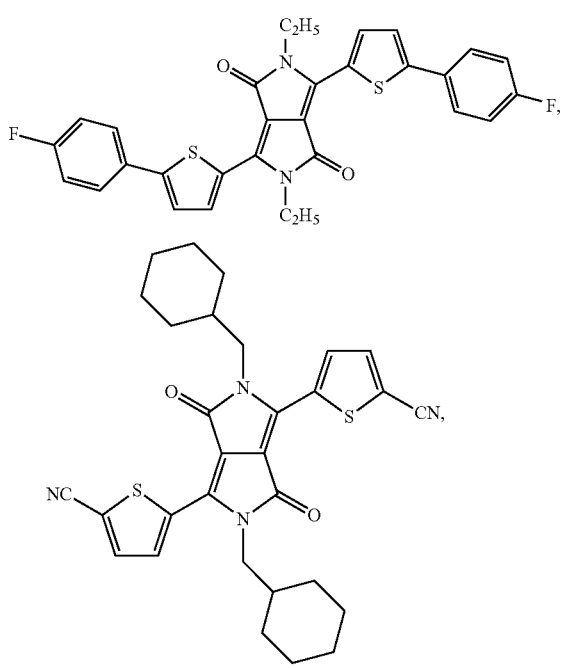

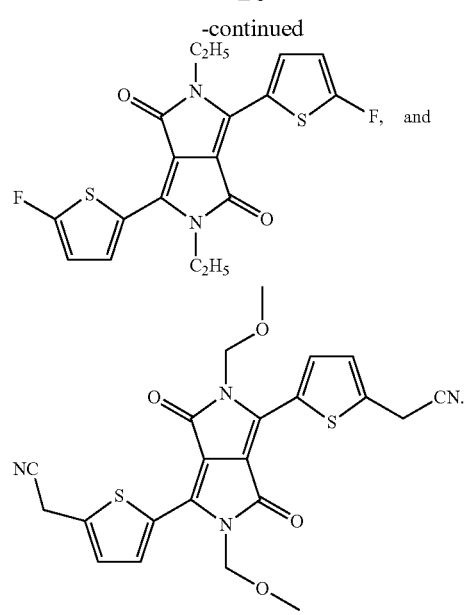

JP2007266285 relates to OFETs which use, as semiconductors, compounds of

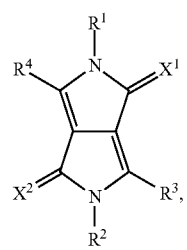

(I)

where X¹, X²=O, S or Se; and R¹-R⁴=H, or aliph. hydrocarbon or arom. groups which may be substituted. The following compounds were explicitly disclosed:

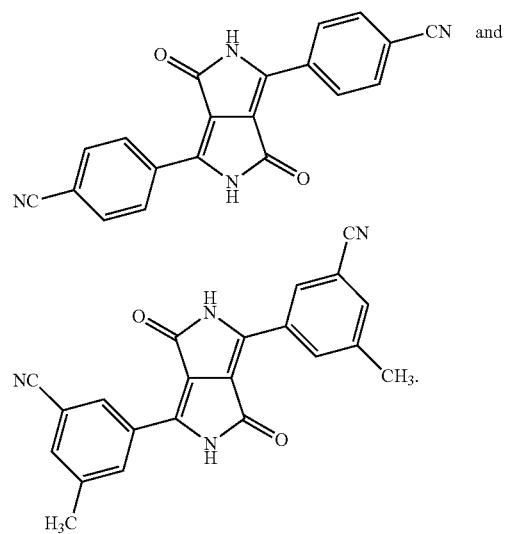

JP2008078247 relates to an organic transistor having an di-Ph pyrrolopyrroledione organic semiconductor compound, formed by vacuum vapor deposition. The following compounds were explicitly disclosed:

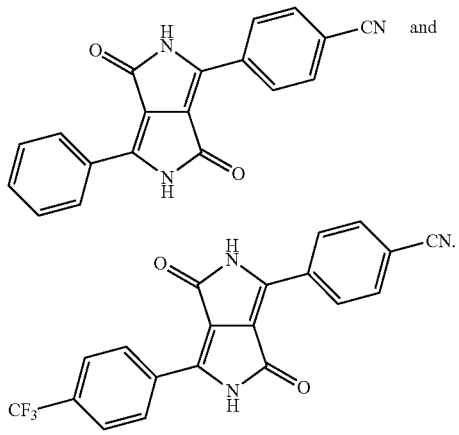

EP2034537A2 relates to a thin film transistor device comprising a semiconductor layer, the semiconductor layer comprising a compound comprising a chemical structure represented by:

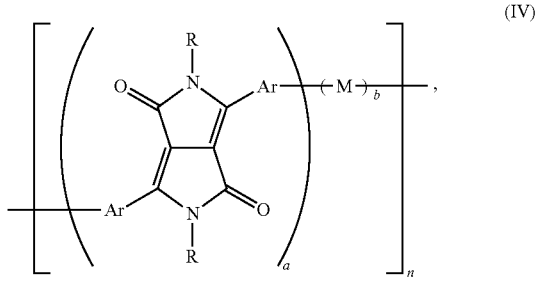

wherein each R is independently selected from hydrogen, an optionally substituted hydrocarbon, and a hetero-containing group; each Ar is independently selected from optionally substituted aryl and heteroaryl groups; each M is an optional, conjugated moiety; a represents a number that is at least 1; b represents a number from 0 to 20; and n represents a number that is at least 1.

WO2009/047104 relates to a compound of the formula I

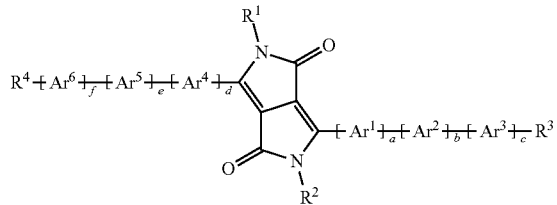

wherein $R^1$ and $R^2$ are independently of each other an aliphatic, cycloaliphatic, cycloaliphatic-aliphatic, aromatic, aromatic-aliphatic, heteroaromatic or heteroaromatic-aliphatic group having up to 49 carbon atoms, a and d independently of each other are 0, 1, 2 or 3, $Ar^1$ and $Ar^4$ are independently of each other a bivalent group of the formula II or IV

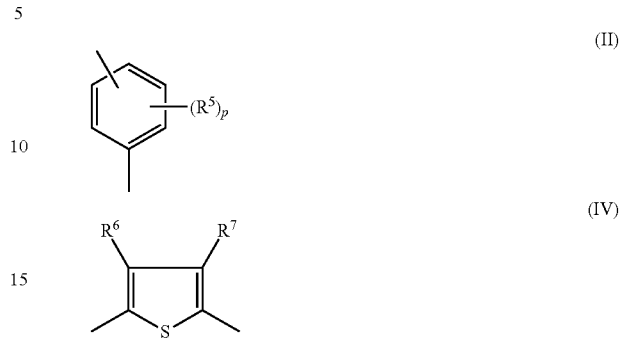

wherein $R^6$ and $R^7$ are as defined below, p represents 0, 1, or 2, $R^5$ is an aliphatic hydrocarbon group having up to 25 carbon atoms, or two vicinal groups $R^5$ together represent alkylene or alkenylene having up to 7 carbon atoms, it being possible that two groups $R^5$ present in the group of formula II differ from each other, b, c, e, and f independently of each other represent 1, 2 or 3, $Ar^2$, $Ar^3$, $Ar^5$, and $Ar^6$ are independently of each other a bivalent group of one of the formulae

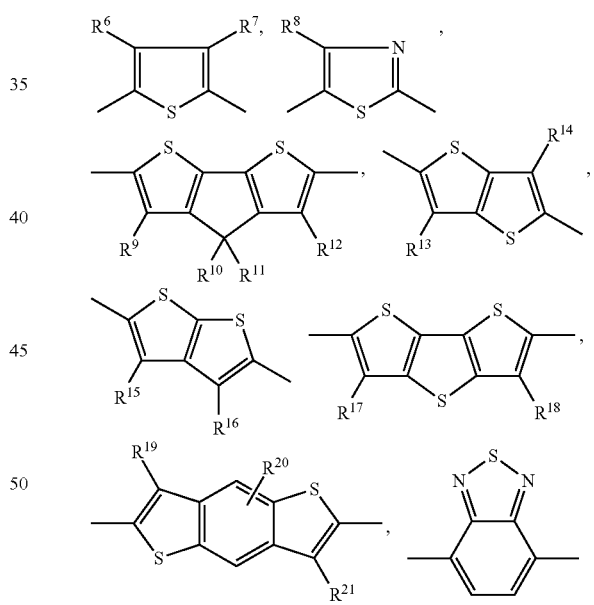

wherein $R^6$, $R^7$, $R^8$, $R^9$, $R^{12}$, $R^{13}$, $R^{15}$, $R^{16}$, $R^{17}$, $R^{18}$, $R^{19}$, $R^{20}$ and $R^{21}$ are independently of each other hydrogen, $C_1$-$C_{25}$alkyl, $C_1$-$C_{18}$alkoxy, $C_6$-$C_{24}$aryl, $C_7$-$C_{25}$aralkyl, or heteroaryl, or $R^6$ and $R^7$ together represent alkylene or alkenylene which may be both bonded via oxygen and/or sulfur to the thienyl residue and which may both have up to 25 carbon atoms, $R^{10}$ and $R^{11}$ are independently of each other hydrogen, $C_1$-$C_{18}$alkyl, $C_6$-$C_{24}$aryl, heteroaryl, or $R^{10}$ and $R^{11}$ together represent oxo or form a five or six membered ring, which is unsubstituted or substituted by a) an aliphatic hydrocarbon group having up to 18 carbon atoms, b) $C_1$-$C_{18}$alkoxy or $C_2$-$C_{18}$alkylenedioxy in both of which carbon atoms which are not adjacent to oxygen may be replaced by oxygen, or c) $C_6$-$C_{24}$aryl, $C_7$-$C_{25}$aralkyl, heteroaryl, $C_3$-$C_{12}$cycloalkyl or $C_4$-$C_{12}$cycloalkyl-alkyl, and $R^3$ and $R^4$ are independently of each other a group of one of the formulae

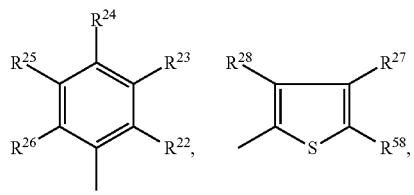

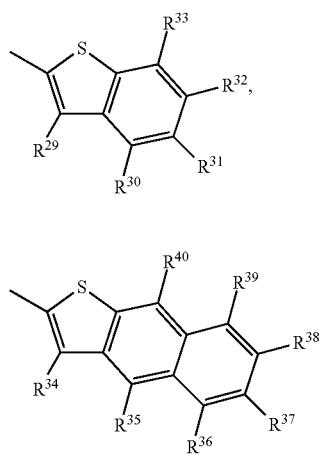

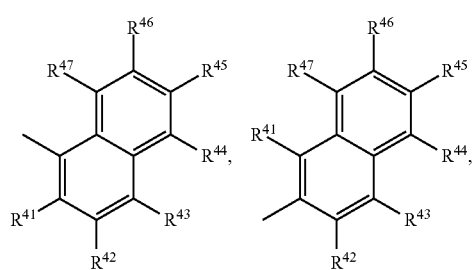

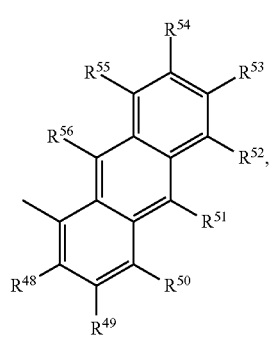

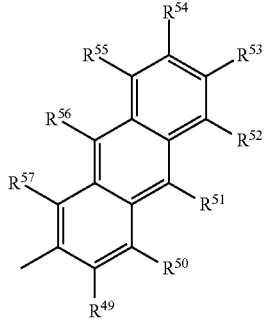

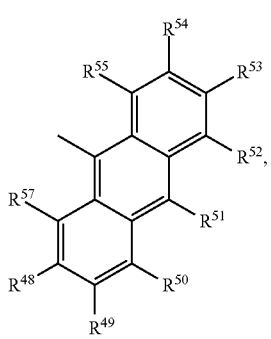

wherein $R^{22}$ to $R^{26}$ and $R^{29}$ to $R^{58}$ represent independently of each other hydrogen, an aliphatic hydrocarbon group having up to 25 carbon atoms, alkoxy or alkenyloxy having up to 18 carbon atoms, halogen, a cycloaliphatic, cycloaliphatic-aliphatic, aromatic, aromatic-aliphatic, heteroaromatic or heteroaromatic-aliphatic group having up to 25 carbon atoms, or a group of the formula

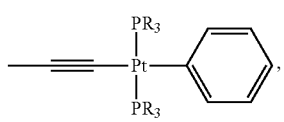

wherein R represents an aliphatic hydrocarbon group having up to 12 carbon atoms, or two groups $R^{22}$ to $R^{26}$ and $R^{29}$ to $R^{57}$ which are in the neighborhood of each other, together represent alkylene or alkenylene having up to 8 carbon atoms, thereby forming a ring, and $R^{27}$ and $R^{28}$ are independently of each other hydrogen, $C_1$-$C_{25}$alkyl, $C_1$-$C_{18}$alkoxy, $C_6$-$C_{24}$aryl, $C_7$-$C_{25}$aralkyl, heteroaryl, or a group of the formula (III) shown above, wherein R represents an aliphatic hydrocarbon group having up to 12 carbon atoms, or $R^{27}$ and $R^{28}$ together or $R^{27}$ and $R^{58}$ together represent alkylene or alkenylene which may be both bonded via oxygen and/or sulfur to the thienyl residue and which may both have up to 25 carbon atoms.

PCT/EP2010/053655 relates to compounds of the formula
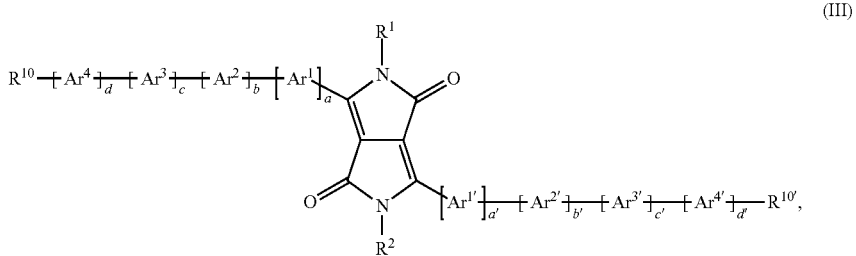
(III)
wherein a, a', b, b', c, c', d, d', $R^1$, $R^2$, $Ar^1$, $Ar^{1'}$, $Ar^2$, $Ar^{2'}$, $Ar^3$, $Ar^{3'}$, $Ar^4$ and $Ar^{4'}$ are as defined in claim 1,
$R^{10}$ and $R^{10'}$ are independently of each other hydrogen, halogen, $C_1$-$C_{25}$alkyl, $C_1$-$C_{25}$alkoxy, or a group of one of the formulae IVa to IVi,
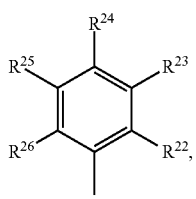
(IVa)
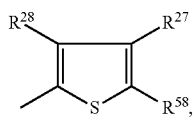
(IVb)
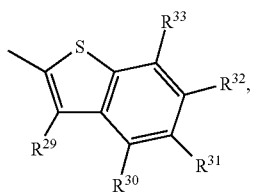
(IVc)
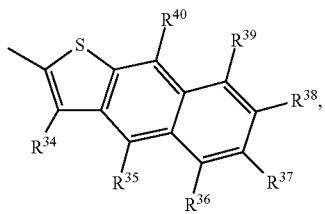
(IVd)
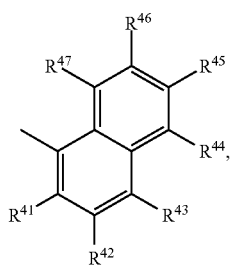
(IVe)
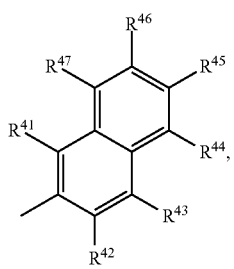
(IVf)
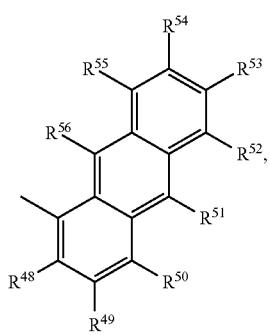
(IVg)
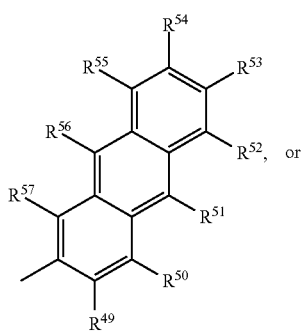
(IVh) or
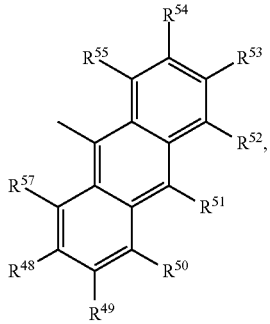
(IVi)

wherein R²² to R²⁶ and R²⁹ to R⁵⁸ represent independently of each other H, halogen, $C_1$-$C_{25}$alkyl, $C_1$-$C_{25}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, a $C_4$-$C_{18}$cycloalkyl group, a $C_4$-$C_{18}$cycloalkyl group, which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or $C_7$-$C_{25}$aralkyl, which is substituted by G, R²⁷ and R²⁸ are independently of each other hydrogen, $C_1$-$C_{25}$alkyl, or $C_7$-$C_{25}$aralkyl, or R²⁷ and R²⁸ together represent alkylene or alkenylene which may be both bonded via oxygen and/or sulfur to the thienyl residue and which may both have up to 25 carbon atoms, D is —CO—, —COO—, —S—, —O—, or —NR¹¹²—, E is $C_1$-$C_8$thioalkoxy, $C_1$-$C_8$alkoxy, CN, —NR¹¹²R¹¹³, —CONR¹¹²R¹¹³, or halogen, G is E, or $C_1$-$C_{18}$alkyl, and R¹¹² and R¹¹³ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; with the proviso that the following compound

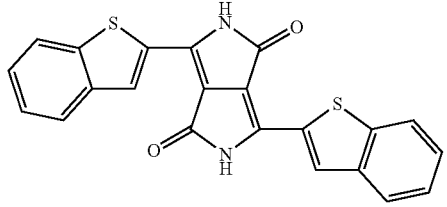 [SMILES: O=C1NC(c2cc3ccccc3s2)=C2C(=O)NC(c3cc4ccccc4s3)=C12]

is excluded.

US2010/0032657 describes an org. transistor comprising a source electrode, a drain electrode, a gate electrode, and an org. semiconductor layer, characterized in that the organic semiconductor layer comprises a compound represented by the following general formula

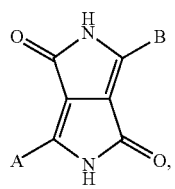

(I)

wherein A and B each independently represent a substituted alkyl group, an unsubstituted alkyl group, a substituted heterocyclic group, an unsubstituted heterocyclic group, a substituted aryl group, or an unsubstituted aryl group; or general formula

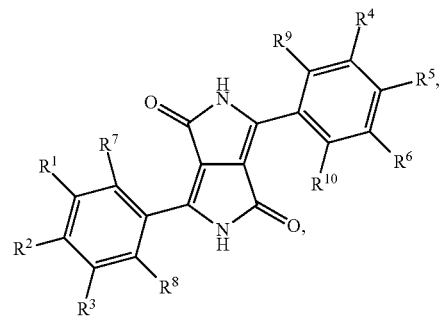

(II)

wherein R¹ to R¹⁰ are each independently a hydrogen atom, a halogen atom, an alkyl group which has 4 or less carbon atoms, an alkyl group which has 4 or less carbon atoms that is substituted with a halogen atom, an alkoxy group which has 4 or less carbon atoms, an alkoxy group which has 4 or less carbon atoms that is substituted with a halogen atom, an amino group which has 4 or less carbon atoms, an amino group which has 4 or less carbon atoms that is substituted with a halogen atom, a nitro group, or a cyano group, and the compound contains at least one halogen atom. Among others the following compounds are explicitly mentioned:

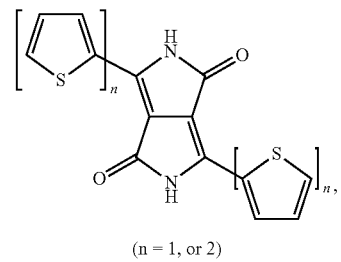

(n = 1, or 2)

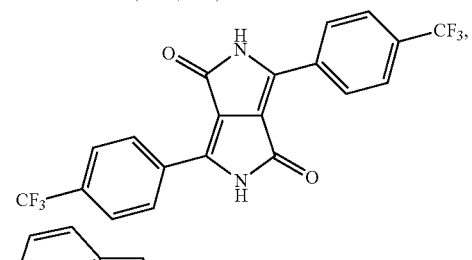

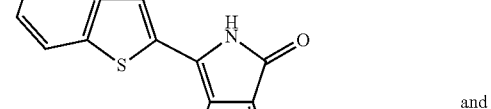

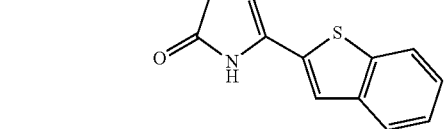

and

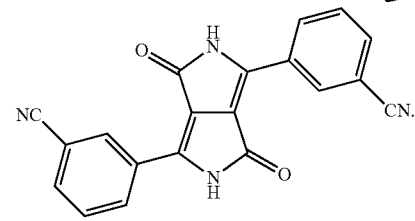

WO2008/013427A1 relates to organic thin film transistors comprising an organic semiconductor layer including an organic semiconductor substance having a functional group that can form a hydrogen bond. Examples of the organic semiconductor substance are represented by compounds of formula

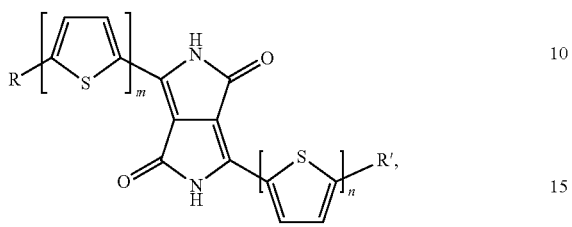

wherein n and m are each independently 0 or a positive integer, and R and R' are each independently any one selected from the group consisting of an alkyl group, an alkoxy group, an acetyl group, an imine group, an ether group, an ester group, a nitrile group, a thioalkoxy group, an amino group, a thioester group, a vinyl group, an aryl group, and a hetero group.

It is the object of the present invention to provide compounds, which show high efficiency of energy conversion, excellent field-effect mobility, good on/off current ratios and/or excellent stability, when used in organic field effect transistors, organic photovoltaics (solar cells) and photodiodes.

Said object has been solved by compounds of the formula

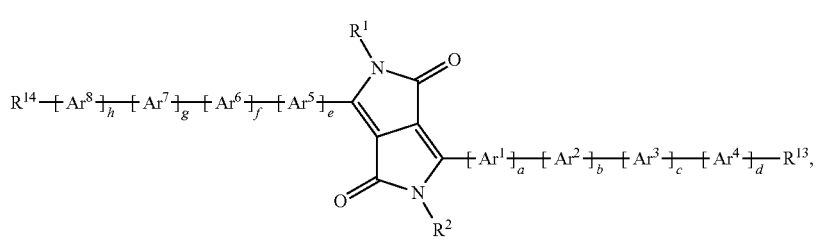
(I)

wherein $R^1$ and $R^2$ may be the same or different and are selected from a $C_1$-$C_{100}$alkyl group, —COOR$^{103}$, a $C_1$-$C_{100}$alkyl group which is substituted by one or more halogen, especially fluorine atoms, hydroxyl groups, nitro groups, —CN, or $C_6$-$C_{24}$aryl groups and/or interrupted by —O—, —COO—, —OCO—, or —S—; a $C_7$-$C_{100}$arylalkyl group, which can be substituted one to five times with $C_1$-$C_8$alkyl, $C_1$-$C_8$alkoxy, —CF$_3$ and/or F, a carbamoyl group, $C_5$-$C_{12}$cycloalkyl, which can be substituted one to three times with $C_1$-$C_8$alkyl and/or $C_1$-$C_8$alkoxy, a $C_6$-$C_{24}$aryl group, in particular phenyl or 1- or 2-naphthyl which can be substituted one to three times with $C_1$-$C_8$alkyl, $C_1$-$C_8$thioalkoxy, and/or $C_1$-$C_8$alkoxy, or pentafluorophenyl, a is 1, 2 or 3, and e is 1, 2 or 3, b, c, d, f, g and h independently of each other represent 0, 1, 2 or 3, $Ar^1$ and $Ar^5$ are independently of each other

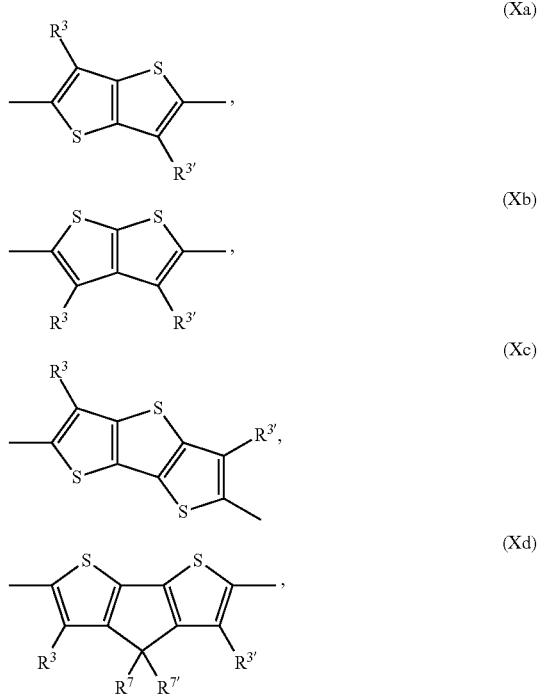

-continued

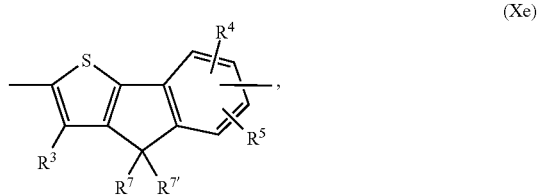

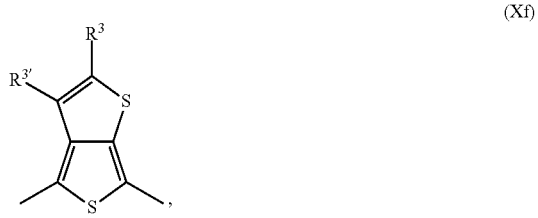

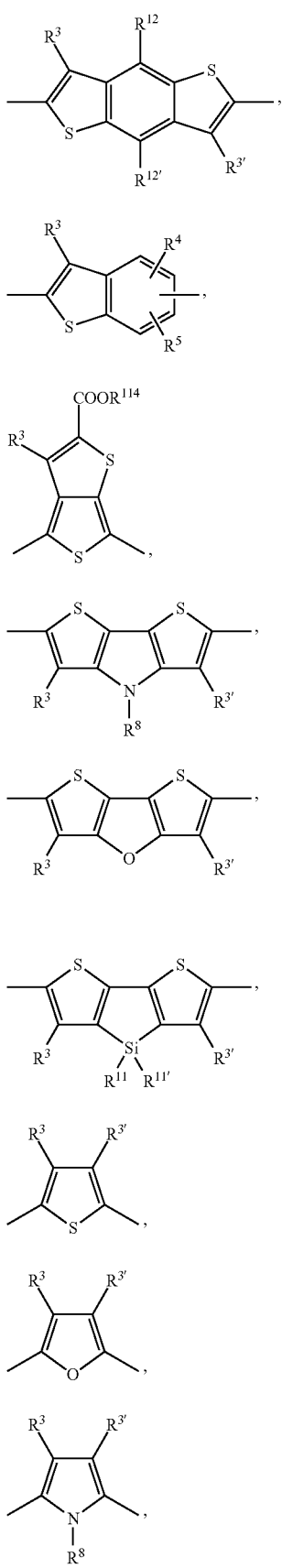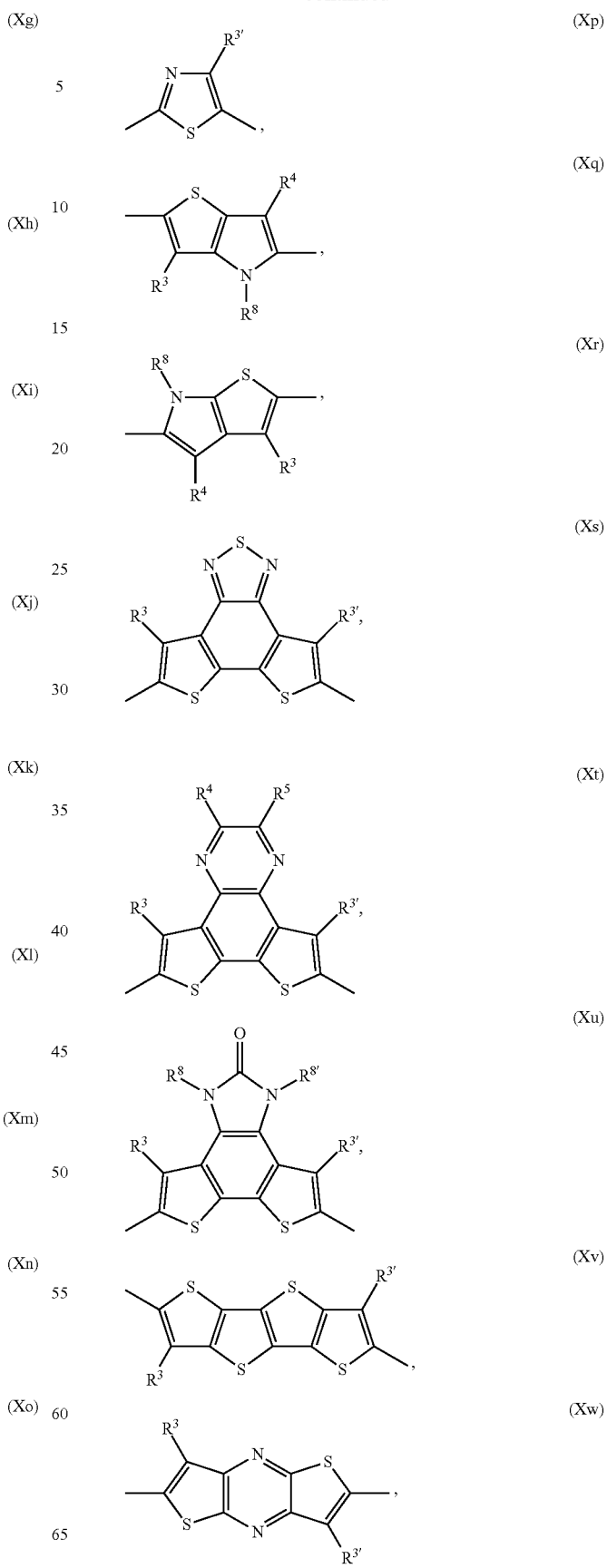

-continued

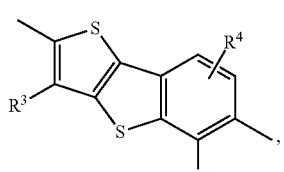
(Xx)

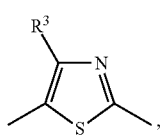
(Xy)

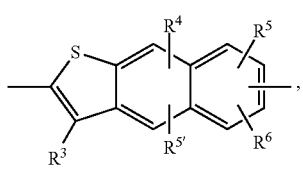
(Xz)

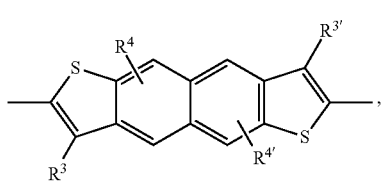
(Xa′)

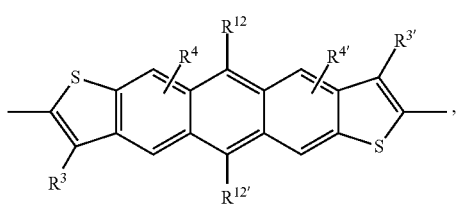
(Xb′)

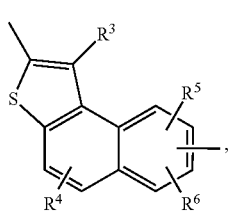
(Xc′)

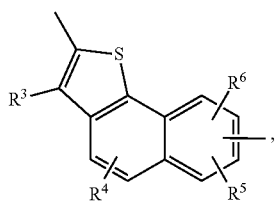
(Xd′)

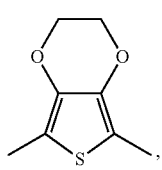
(Xe′)

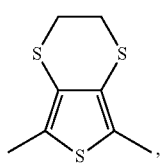
(Xf′)

-continued

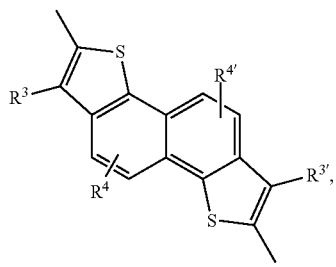
(Xg′)

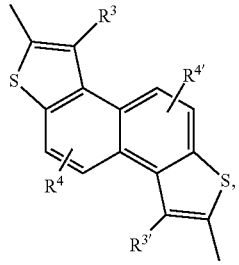
(Xh′)

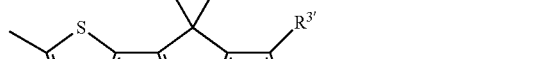
(Xi′)

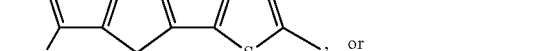
(Xj′), or

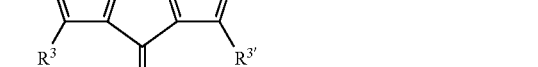
(Xk′)

$R^3$ and $R^{3'}$ are independently of each other hydrogen, halogen, halogenated $C_1$-$C_{25}$alkyl, especially $CF_3$, CN, $C_1$-$C_{25}$alkyl, especially $C_3$-$C_{25}$alkyl, which may optionally be interrupted by one or more oxygen or sulphur atoms; $C_7$-$C_{25}$arylalkyl, or $C_1$-$C_{25}$alkoxy;

$R^4$, $R^{4'}$, $R^5$, $R^{5'}$, $R^6$ and $R^{6'}$ are independently of each other hydrogen, halogen, halogenated $C_1$-$C_{25}$alkyl, especially $CF_3$, CN, $C_1$-$C_{25}$alkyl, especially $C_3$-$C_{25}$alkyl, which may optionally be interrupted by one or more oxygen or sulphur atoms; $C_7$-$C_{25}$arylalkyl, or $C_1$-$C_{25}$alkoxy;

$R^{114}$ is $C_1$-$C_{25}$alkyl, especially $C_3$-$C_{25}$alkyl, which may optionally be interrupted by one, or more oxygen, or sulphur atoms, $R^7$, $R^{7'}$, $R^9$ and $R^{9'}$ are independently of each other hydrogen, $C_1$-$C_{25}$alkyl, especially $C_3$-$C_{25}$alkyl, which may optionally be interrupted by one, or more oxygen, or sulphur atoms; or $C_7$-$C_{25}$arylalkyl, $R^{11}$ and $R^{11'}$ are independently of each other $C_1$-$C_{25}$alkyl group, especially a $C_1$-$C_8$alkyl group, $C_7$-$C_{25}$arylalkyl, or a phenyl group, which can be substituted one to three times with $C_1$-$C_8$alkyl and/or $C_1$-$C_8$alkoxy;

$R^{12}$ and $R^{12'}$ are independently of each other hydrogen, halogen, CN, $C_1$-$C_{25}$alkyl, especially $C_3$-$C_{25}$alkyl, which may optionally be interrupted by one, or more oxygen, or sulphur atoms, $C_1$-$C_{25}$alkoxy, $C_7$-$C_{25}$arylalkyl, or

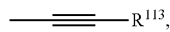

wherein $R^{113}$ is a $C_1$-$C_{18}$alkyl group, or a tri($C_1$-$C_8$alkyl)silyl group;

$Ar^2$, $Ar^3$, $Ar^4$, $Ar^6$, $Ar^7$ and $Ar^8$ have independently of each other the meaning of $Ar^1$, or are a group of formula

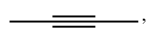
(XII)

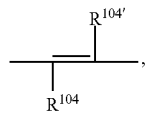
(XIm)

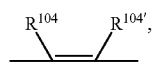
(XIn)

$R^{104}$ and $R^{104'}$ are independently of each other hydrogen, CN, COOR$^{103}$, or a $C_1$-$C_{25}$alkyl group, $R^{103}$ and $R^{103'}$ are independently of each other $C_1$-$C_{100}$alkyl, especially $C_3$-$C_{25}$alkyl, $C_1$-$C_{25}$alkyl interrupted with O, $C_7$-$C_{25}$arylalkyl, $C_6$-$C_{24}$aryl, which may optionally be substituted, or $C_2$-$C_{20}$heteroaryl, which may optionally be substituted, $R^{13}$ and $R^{14}$ are independently of each other hydrogen, CN, an aliphatic hydrocarbon group having up to 25 carbon atoms, alkoxy or alkenyloxy having up to 25 carbon atoms, halogen, a cycloaliphatic, cycloaliphatic-aliphatic, aromatic, aromatic-aliphatic, heteroaromatic or heteroaromatic-aliphatic group having up to 25 carbon atoms, $C_1$-$C_{25}$alkyl group which is substituted by one or more halogen atoms, especially $CF_3$, or a group of one of the formulae

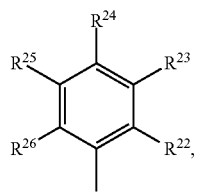
(XI)

(XII)

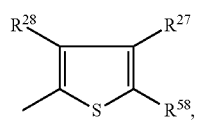
(XIII)

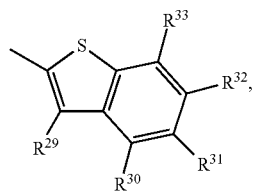
(XIV)

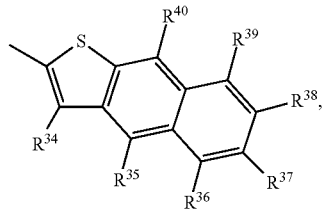
(XV)

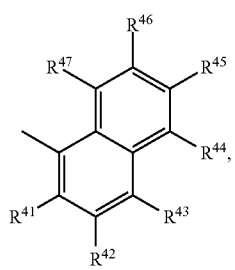
(XVI)

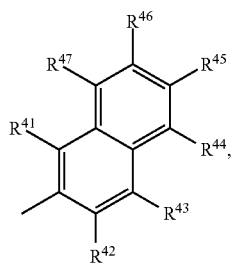
(XVII)

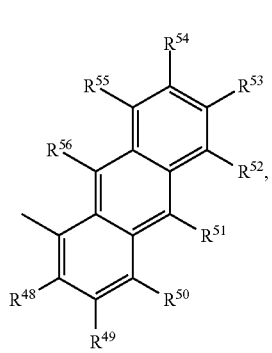
(XVIII)

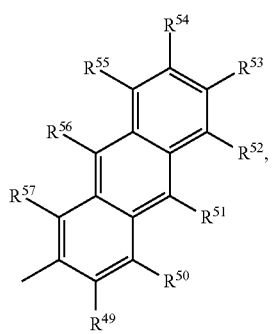

-continued

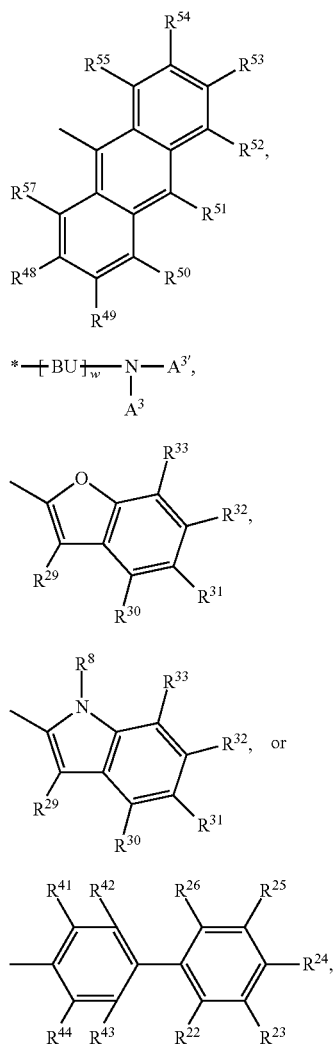

wherein w is 0, or 1, BU is a bridging unit and $A^3$ and $A^{3'}$ are independently of each other a $C_6$-$C_{24}$aryl group, or a $C_2$-$C_{26}$heteroaryl group, which can optionally be substituted, $R^8$ and $R^{8'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_3$-$C_{25}$alkyl, which may optionally be interrupted by one or more oxygen or sulphur atoms; or $C_7$-$C_{25}$arylalkyl, $R^{22}$ to $R^{58}$ represent independently of each other hydrogen, CN, an aliphatic hydrocarbon group having up to 25 carbon atoms, $C_1$-$C_{25}$alkyl group which is substituted by one or more halogen atoms, especially $CF_3$, alkoxy or alkenyloxy having up to 25 carbon atoms, halogen, a cycloaliphatic, cycloaliphatic-aliphatic, aromatic, aromatic-aliphatic, heteroaromatic or heteroaromatic-aliphatic group having up to 25 carbon atoms, or $R^{27}$ and $R^{28}$, or $R^{27}$ and $R^{58}$ together represent alkylene or alkenylene which may be both bonded via oxygen and/or sulfur to the thienyl residue and which may both have up to 25 carbon atoms; with the proviso, that at least one of the groups $Ar^1$, $Ar^2$, $Ar^3$, $Ar^4$, $Ar^5$, $Ar^6$, $Ar^7$ and $Ar^8$ is substituted by CN, and/or $R^{13}$ and $R^{14}$ represent CN, or a substituent, which is substituted by CN.

Advantageously, the compounds of the present invention, or an organic semiconductor material, layer or component, comprising the compounds of the present invention can be used in organic photovoltaics (solar cells) and photodiodes, or in an organic field effect transistor (OFET).

BRIEF DESCRIPTION OF THE DRAWINGS

FIG. 1 shows output and transfer characteristics for bottom-gate top-contact TFT with

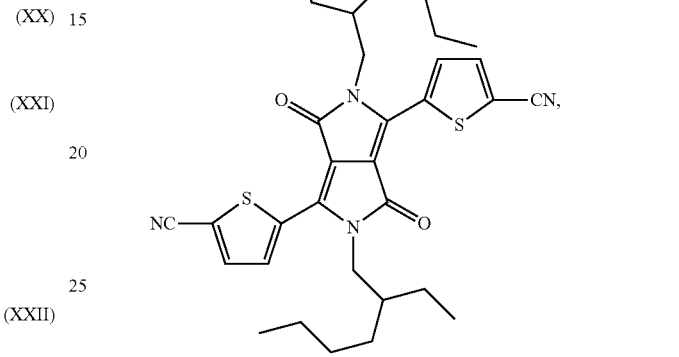

(A-1)

the synthesis of which is described in Example 1. The novel type of efficient p-channel material, compound A-1, exhibits high hole-mobilities and on/off-ratios in vacuum deposited TFTs.

$R^1$ and $R^2$ may be different, but are preferably the same; and are preferably selected from a $C_1$-$C_{100}$alkyl group, a $C_1$-$C_{100}$alkyl group which is substituted by one or more halogen atoms, —CN, or $C_6$-$C_{18}$aryl groups and/or interrupted by —O—, —COO—, —OCO—, or —S—; a $C_7$-$C_{25}$arylalkyl group, which can be substituted one to five times with $C_1$-$C_8$alkyl, $C_1$-$C_8$alkoxy, —$CF_3$ and/or F; and pentafluorophenyl.

More preferably $R^1$ and $R^2$ are selected from a $C_1$-$C_{38}$alkyl group, a $C_1$-$C_{38}$alkyl group which is substituted by one or more halogen atoms, especially a F containing $C_2$-$C_{36}$alkyl group, very especially $CH_2C_nF_{2n+1}$ (n=1 to 10); a $C_7$-$C_{25}$arylalkyl group, which can be substituted one to five times with $C_1$-$C_8$alkyl, $C_1$-$C_8$alkoxy, —$CF_3$ and/or F, especially

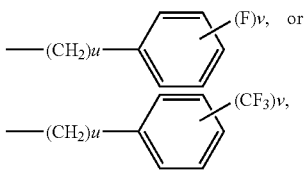

u is 1, or 2, v is 1 to 5; and pentafluorophenyl.

In a preferred embodiment $R^1$ and $R^2$ are a $C_1$-$C_{38}$alkyl group, especially a $C_2$-$C_{12}$alkyl group, such as, for example, methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl 2-ethylhexyl, n-nonyl, decyl, undecyl, and n-dodecyl.

Advantageously, the groups $R^1$ and $R^2$ can be represented by formula

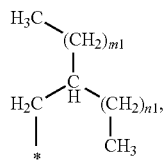

wherein $m1=n1+2$ and $m1+n1 \leq 24$. Chiral side chains, such as $R^1$ and $R^2$, can either be enantiomerically pure, homochiral, or racemic, which can influence the morphology of the polymers.

In another preferred embodiment $R^1$ and $R^2$ are a F containing $C_2$-$C_{36}$alkyl group, especially $CH_2C_nF_{2n+1}$ (n=1 to 10), such as, for example, $CH_2CF_3$, $CH_2C_2F_5$, $CH_2C_3F_7$, $CH_2C_4F_9$, $CH_2C_5F_{11}$, $CH_2C_6F_{13}$ and $CH_2C_{10}F_{21}$.

In another preferred embodiment $R^1$ and $R^2$ are a $C_7$-$C_{25}$arylalkyl group, which can be substituted one to five times with $C_1$-$C_8$alkyl, $C_1$-$C_8$alkoxy and/or F. In said embodiment groups of formula

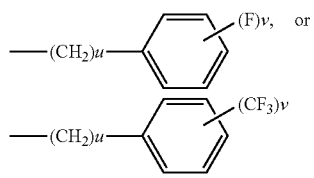

are more preferred, wherein
u is 1, or 2, and v is 1 to 5. Examples are

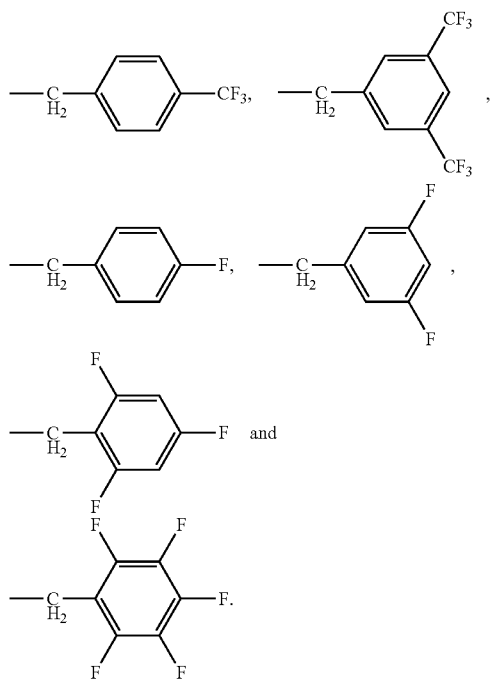

Preferably, $R^3$ and $R^{3'}$ are independently of each other hydrogen, halogen, $CF_3$, cyano, $C_1$-$C_{25}$alkyl or $C_1$-$C_{25}$alkoxy; more preferably $CF_3$, cyano or $C_1$-$C_{25}$alkyl; most preferred hydrogen, or $C_1$-$C_{25}$alkyl;

Preferably, $R^{104}$ and $R^{104'}$ are independently of each other hydrogen, cyano or a $C_1$-$C_{25}$alkyl group, more preferably hydrogen, or a $C_1$-$C_{25}$alkyl group, most preferred hydrogen.

Preferably, $R^4$, $R^{4'}$, $R^5$, $R^{5'}$, $R^6$ and $R^{6'}$ are independently of each other hydrogen, halogen, $CF_3$, cyano, $C_1$-$C_{25}$alkyl or $C_1$-$C_{25}$alkoxy, more preferably hydrogen, $CF_3$, cyano or $C_1$-$C_{25}$alkyl; most preferred hydrogen, or $C_1$-$C_{25}$alkyl.

Preferably $R^7$, $R^{7'}$, $R^9$ and $R^{9'}$ are independently of each other hydrogen, $C_1$-$C_{25}$alkyl, more preferably $C_4$-$C_{25}$alkyl.

Preferably, $R^8$ and $R^{8'}$ are independently of each other hydrogen, $C_1$-$C_{25}$alkyl, $C_1$-$C_{25}$alkyl, which may optionally be interrupted by one or more oxygen or sulphur atoms; or $C_7$-$C_{25}$arylalkyl, more preferably hydrogen, or $C_1$-$C_{25}$alkyl.

Preferably, $R^{11}$ and $R^{11'}$ are independently of each other a $C_1$-$C_{25}$alkyl group, especially a $C_1$-$C_8$alkyl group, or phenyl; more preferably a $C_1$-$C_8$alkyl group.

Preferably, $R^{12}$ and $R^{12'}$ are independently of each other hydrogen, $C_1$-$C_{25}$alkyl, $C_1$-$C_{25}$alkoxy, or $-\!\!\equiv\!\!-R^{13}$, wherein $R^{13}$ is a $C_1$-$C_{18}$alkyl group, or a tri($C_1$-$C_8$alkyl)silyl group, more preferably hydrogen, $C_1$-$C_{25}$alkyl, or $C_1$-$C_{25}$alkoxy.

Preferably $Ar^1$ and $Ar^5$ are independently of each other a group of formula (Xa), (Xb), (Xc), (Xd), (Xe), (Xg), (Xh), (Xk), (Xl), (Xm), (Xn), (Xo), (Xp), (Xv), (Xx), (Xy), (Xz), (Xa'), (Xb'), (Xc'), (Xd'), (Xe'), (Xf'), (Xg'), (Xh'), or (Xi'), more preferably a group of formula (Xa), (Xc), (Xg), (Xh), (Xm), (Xn), (Xo), (Xp), (Xy), (Xe'), or (Xf'), still more preferably a group of formula (Xa), (Xc), (Xm), (Xn), or (Xo), most preferred a group of formula (Xa), (Xm), or (Xn), especially (Xm).

More preferably, $Ar^1$ and $Ar^5$ are independently of each other

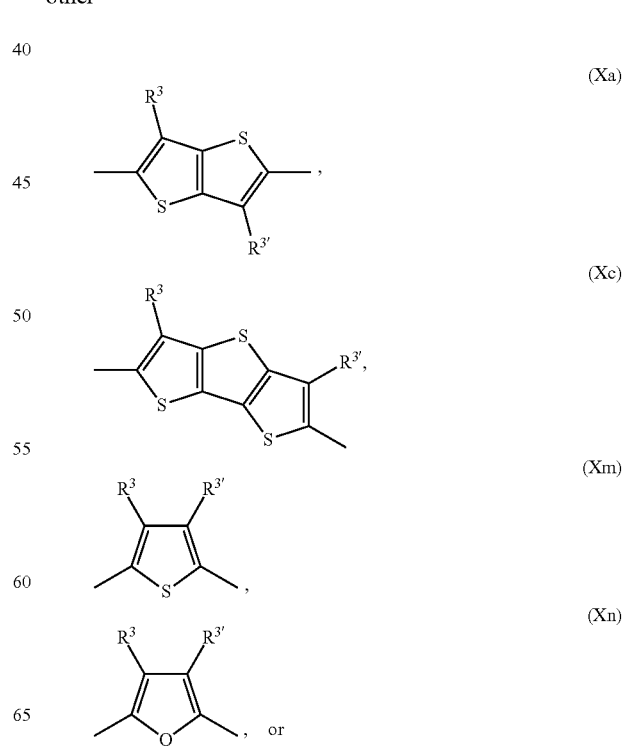

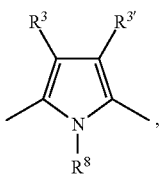 (Xo)

wherein $R^3$ and $R^{3'}$ are independently of each other hydrogen, halogen, $CF_3$, CN, $C_1$-$C_{25}$alkyl or $C_1$-$C_{25}$alkoxy, and $R^8$ is hydrogen or $C_1$-$C_{25}$alkyl, especially $C_3$-$C_{25}$alkyl, most preferably $Ar^1$ and $Ar^5$ are independently of each other

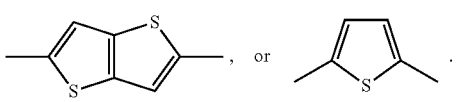

Preferably, $Ar^2$, $Ar^3$, $Ar^4$, $Ar^6$, $Ar^7$ and $Ar^8$ are independently of each other a group of formula (Xa), (Xb), (Xc), (Xd), (Xe), (Xg), (Xh), (Xk), (Xl), (Xm), (Xn), (Xo), (Xp), (Xv), (Xx), (Xy), (Xz), (Xa'), (Xb'), (Xc'), (Xd'), (Xe'), (Xf'), (Xg'), (Xh'), or (Xi'), more preferably a group of formula (Xa), (Xc), (Xg), (Xh), (Xm), (Xn), (Xo), (Xp), (Xy), (Xe'), or (Xf'), still more preferably a group of formula (Xa), (Xc), (Xm), (Xn), or (Xo), most preferred a group of formula (Xa), (Xm), or (Xn), especially (Xm).

More preferably $Ar^2$, $Ar^3$, $Ar^4$, $Ar^6$, $Ar^7$ and $Ar^8$ are independently of each other

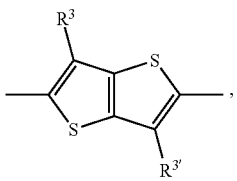 (Xa)

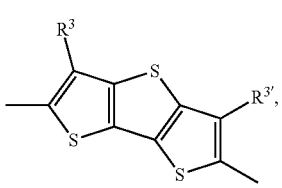 (Xc)

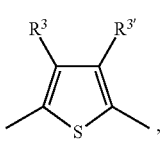 (Xm)

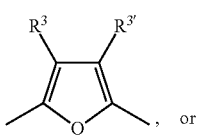 (Xn)

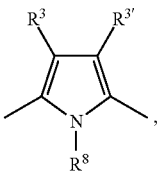 (Xo)

wherein $R^3$ and $R^{3'}$ are independently of each other hydrogen, halogen, $CF_3$, CN, $C_1$-$C_{25}$alkyl or $C_1$-$C_{25}$alkoxy, and $R^8$ is hydrogen or $C_1$-$C_{25}$alkyl, most preferably $Ar^2$, $Ar^3$, $Ar^4$, $Ar^6$, $Ar^7$ and $Ar^8$ are independently of each other

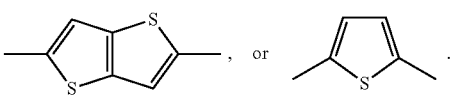

Preferably the compound of formula I is a compound of formula

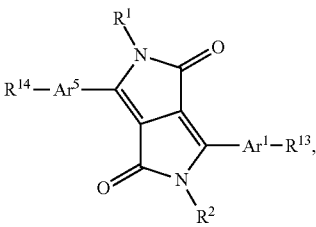 (Ia)

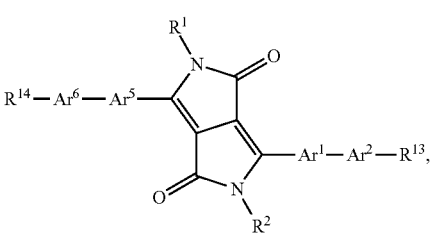 (Ib)

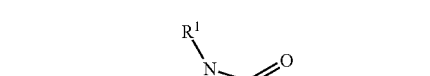

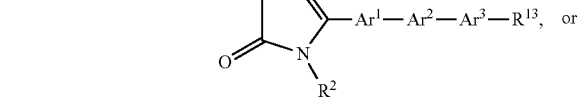 (Ic)

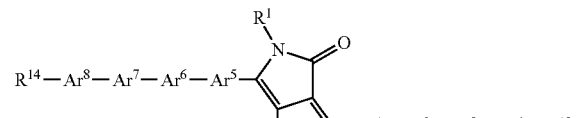 (Id)

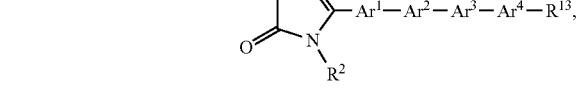

wherein
$R^1$, $R^2$, $R^{13}$, $R^{14}$, $Ar^1$, $Ar^2$, $Ar^3$, $Ar^4$, $Ar^5$, $Ar^6$, $Ar^7$ and $Ar^8$ are as defined above.

$R^{13}$ and $R^{14}$ are preferably CN, or

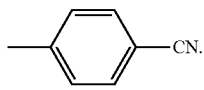

In a preferred embodiment the present invention is directed to compounds of formula

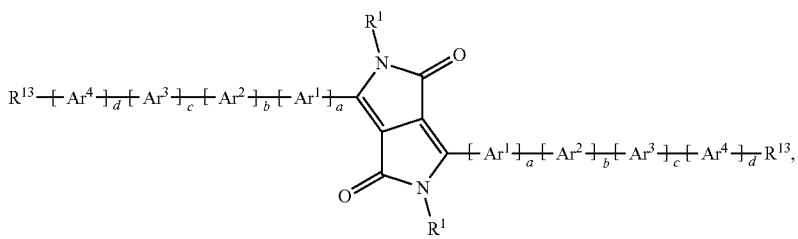

wherein $R^1$ is a $C_1$-$C_{38}$alkyl group, especially a $C_2$-$C_{12}$alkyl group, a F containing $C_2$-$C_{36}$alkyl group, especially $CH_2C_nF_{2n+1}$ (n=1 to 10), o is an integer of 1 to 5, and p is an integer of 1 to 5, or a $C_7$-$C_{25}$arylalkyl group, which can be substituted one to five times with $C_1$-$C_8$alkyl, $C_1$-$C_8$alkoxy and/or F, especially

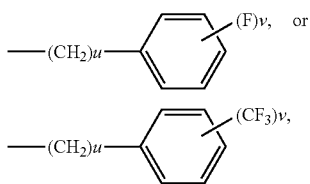

u is 1, or 2, and v is 1 to 5;

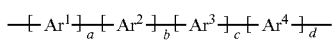

is a group of formula, or

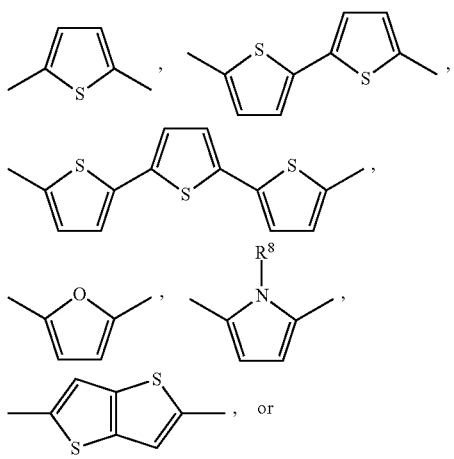

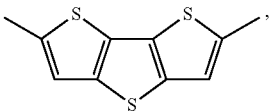

and $R^{13}$ is CN, or

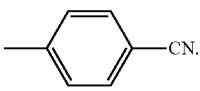

In a particularly preferred embodiment the present invention is directed to compounds of formula

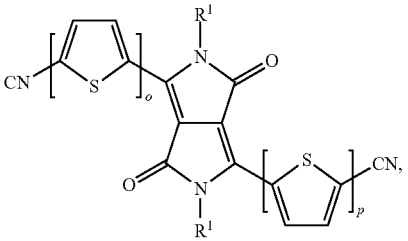

wherein $R^1$ is a $C_1$-$C_{38}$alkyl group, especially a $C_2$-$C_{12}$alkyl group, a F containing $C_2$-$C_{36}$alkyl group, especially $CH_2C_nF_{2n+1}$ (n=1 to 10), o is an integer of 1 to 5, and p is an integer of 1 to 5, or a $C_7$-$C_{25}$arylalkyl group, which can be substituted one to five times with $C_1$-$C_8$alkyl, $C_1$-$C_8$alkoxy and/or F, especially

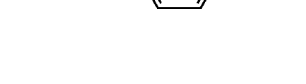

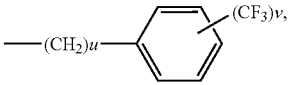

u is 1, or 2, and v is 1 to 5.

In another particularly preferred embodiment the present invention is directed to compounds of the formula (IIIa)
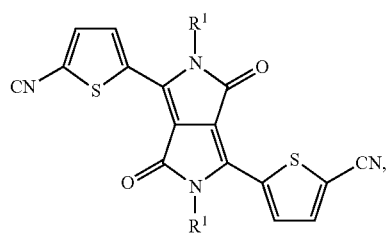
(IIIb)
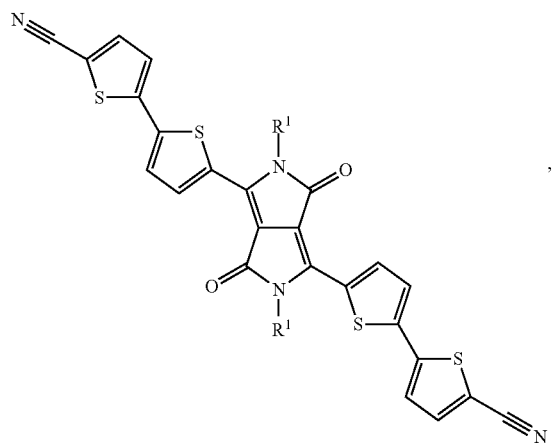
(IIIc)
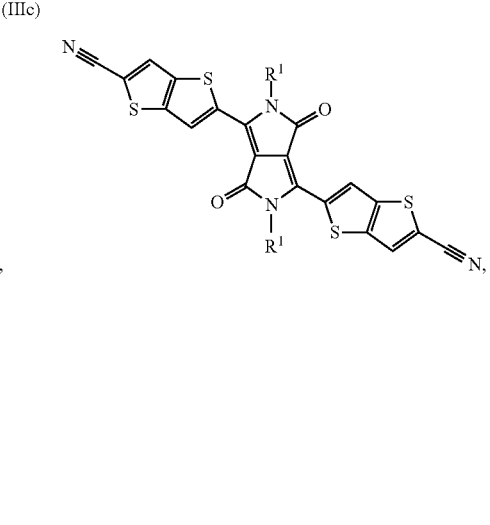
(IIId)
(IIIe)
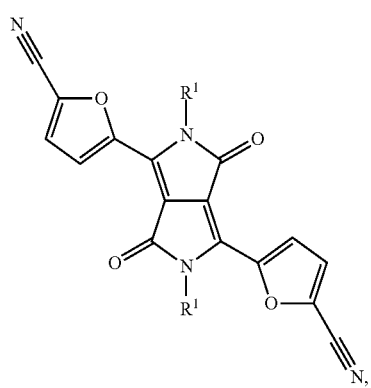
(IIIf)
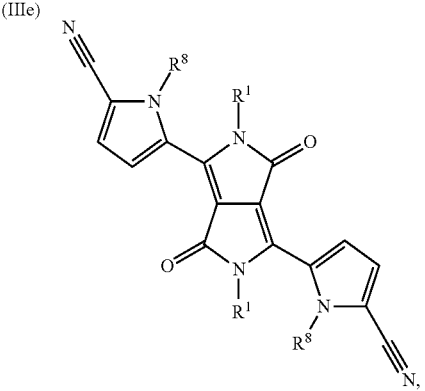

-continued

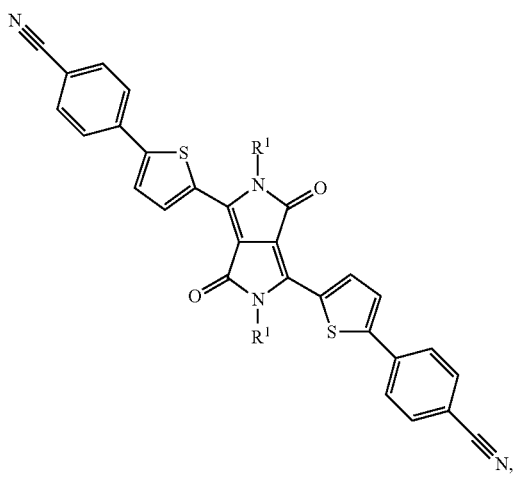
(IIIg)

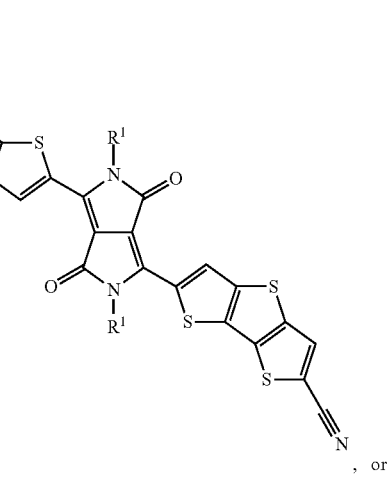
(IIIh)

, or

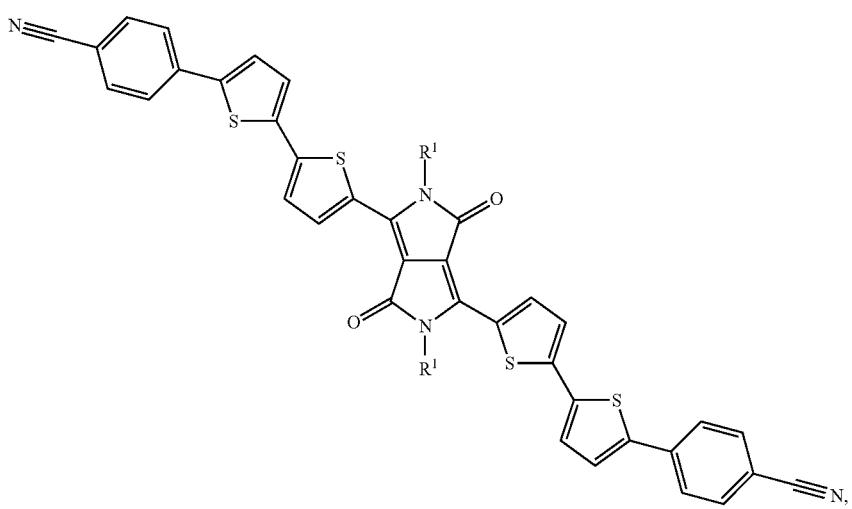
(IIIi)

wherein R¹ is a $C_1$-$C_{38}$alkyl group, especially $C_2$-$C_{12}$alkyl group, such as, for example, methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl 2-ethylhexyl, n-nonyl, decyl, undecyl, and n-dodecyl, a F containing $C_2$-$C_{36}$alkyl group, especially $CH_2C_nF_{2n+1}$ (n=1 to 10), or

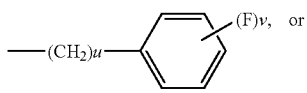

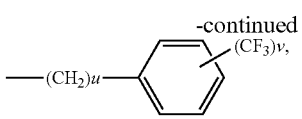

u is 1, or 2, v is 1 to 5, and R⁸ is hydrogen or $C_1$-$C_{25}$alkyl.

Compounds of formula IIIf are less preferred than compounds of formula IIIa to IIIe and IIIg to IIIi, wherein compounds of formula IIIa to IIIe are particularly preferred and compounds of formula IIIa, IIId and IIIe are most preferred.

At present most preferred are compounds A-1 to A-11 and A-13 to A-17 and A-19, which are depicted in claim 10. In further embodiments of the present invention compound (A-18)
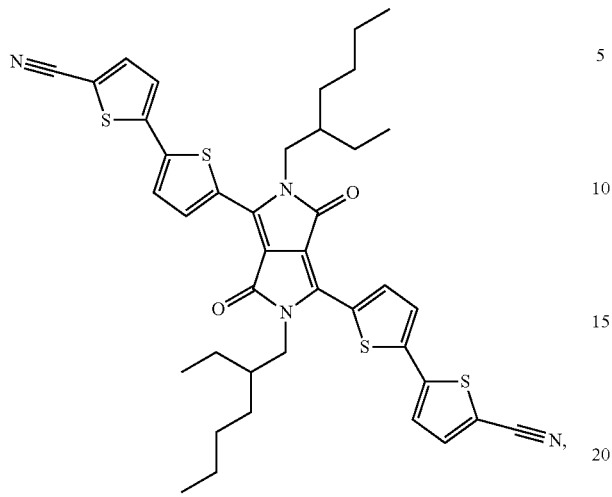
or compound
(I''')
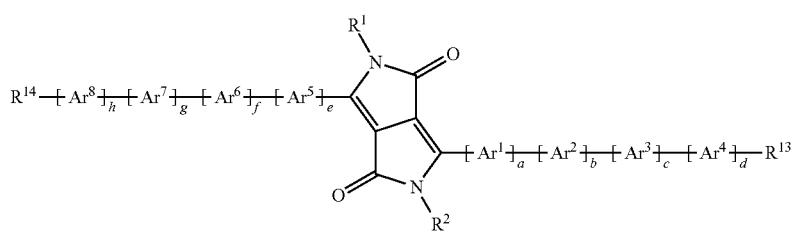
are preferred.
Compounds of formula
(A-20)
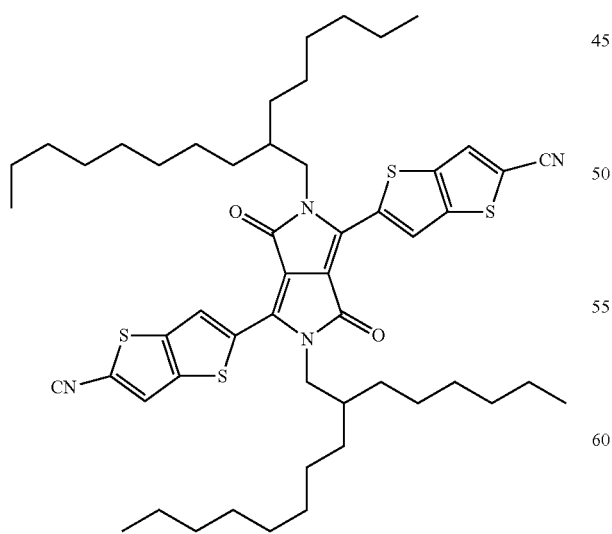
can be prepared by a process, which comprises reacting a compound of formula

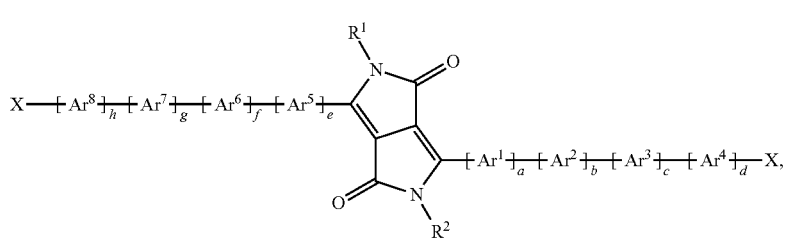
(II)

with copper(I)cyanide. Compounds of formula

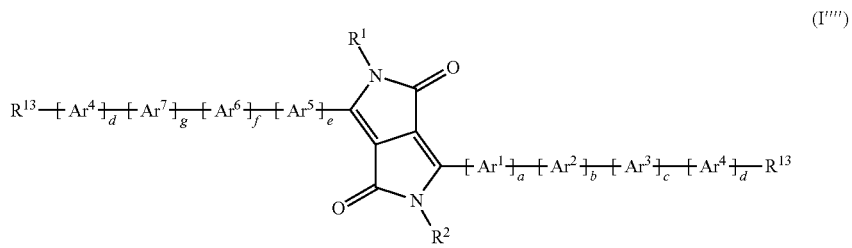
(I'''')

can be prepared by a process, which process comprises reacting a compound of formula

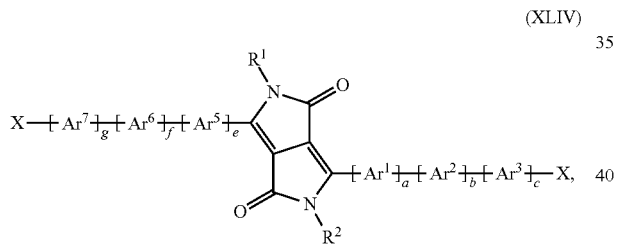
(XLIV)

with an equimolar amount of a diboronic acid or diboronate corresponding to formula $X^{11}$-$A^2$-$R^{13}$ in a solvent and in the presence of a catalyst, or with an equimolar amount of an organo tin compound corresponding to formula $X^{11'}$-$A^2$-$R^{13}$.

The reaction of a compound of formula II with copper(I) cyanide is carried out in a suitable solvent, like dimethylforamide (DMF) and is carried out at a temperature from about room temperature to about 180° C., preferably from about 100° C. to about 170° C., e.g. at 130° C.

Compounds of formula can be prepared by a process, which comprises reacting a compound of formula

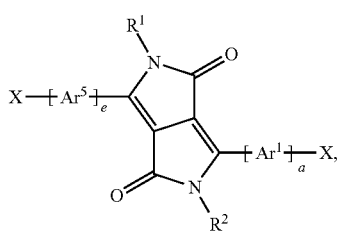
(XLII)

with an equimolar amount of a diboronic acid or diboronate corresponding to formula $X^{11}$-A-$R^{13}$ in a solvent and in the presence of a catalyst; or
with an equimolar amount of an organo tin compound corresponding to formula $X^{11'}$-A-$R^{13}$.

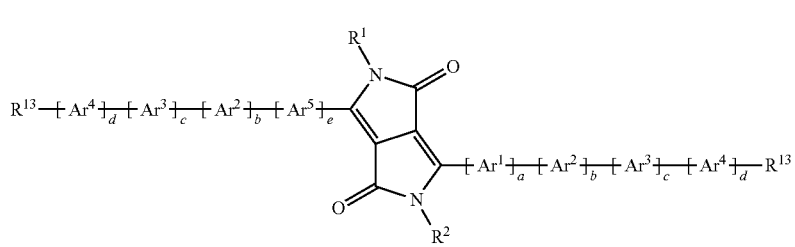
(I')

Compounds of formula

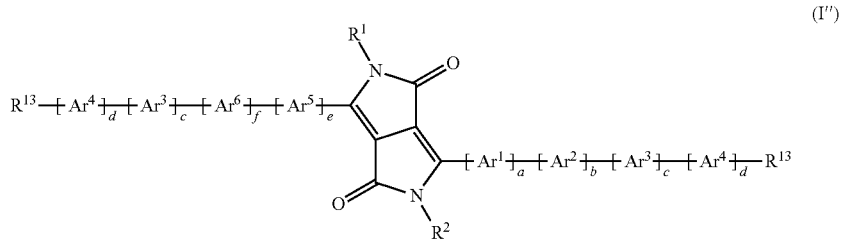

(I'')

can be prepared by a process, which comprises reacting a compound of formula

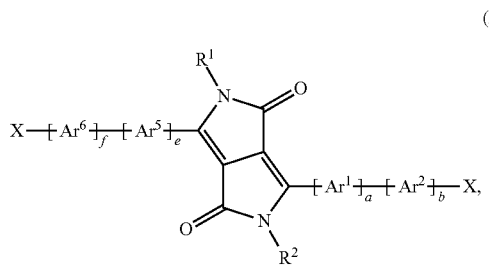

(XLIII)

with an equimolar amount of a diboronic acid or diboronate corresponding to formula $X^{11}$-$A^1$-$R^{13}$ in a solvent and in the presence of a catalyst; or
with an equimolar amount of an organo tin compound corresponding to formula $X^{11'}$-$A^1$-$R^{13}$.

$X^{11}$ is independently in each occurrence —B(OH)$_2$, —B(OY$^1$)$_2$,

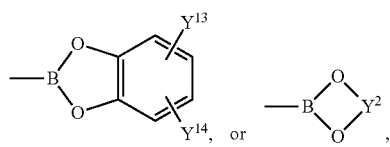

wherein $Y^1$ is independently in each occurrence a $C_1$-$C_{18}$alkyl group and $Y^2$ is independently in each occurrence a $C_2$-$C_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{18}$alkyl group, especially —C(CH$_3$)$_2$C(CH$_3$)$_2$—, —C(CH$_3$)$_2$CH$_2$C(CH$_3$)$_2$—, or —CH$_2$C(CH$_3$)$_2$CH$_2$—, and $Y^{13}$ and $Y^{14}$ are independently of each other hydrogen, or a $C_1$-$C_{18}$alkyl group, in a solvent and in the presence of a catalyst.

The Suzuki reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A condensation reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252.

As illustrated above the compounds of the present invention can also be sythesized by the Stille coupling (see, for example, Babudri et al, J. Mater. Chem., 2004, 14, 11-34; J. K. Stille, Angew. Chemie Int. Ed. Engl. 1986, 25, 508). In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours.

$X^{11'}$ is independently in each occurrence —SnR$^{207}$R$^{208}$R$^{209}$, R$^{207}$, R$^{208}$ and R$^{209}$ are identical or different and are H or $C_1$-$C_6$alkyl, or two of the groups R$^{207}$, R$^{208}$ and R$^{209}$ form a ring and these groups are optionally branched.

In formula I''' and I'''' $R^{13}$ and $R^{14}$ are CN. In formula I' and I'' $R^{13}$ and $R^{14}$ are as defined above and are preferably CN.

A is a group of formula

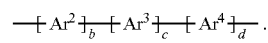

$A^1$ is a group of formula

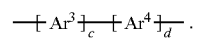

$A^2$ is a group of formula

X is Cl, Br, or I; a, b, c, d, e, f, g, h, $R^1$, $R^2$, $Ar^1$, $Ar^2$, $Ar^3$, $Ar^4$, $Ar^5$, $Ar^6$, $Ar^7$ and $Ar^8$ are as defined above.

In the above described Suzuki and stille couplings the DPP compounds may alternatively comprise the diboronic acid, or diboronate, or organo tin functionalities, $X^{11}$ and $X^{11'}$, and the groups A, $A^1$ and $A^2$ may comprise the halogen functionality, X.

As illustrated above the compounds of the formula I can be manufactured by known methods.

A possible route of manufacture starts from a compound of the formula

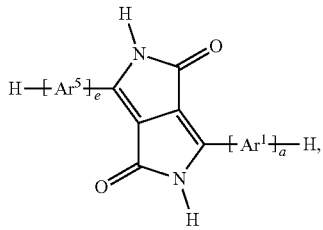
(XXXIV)

wherein a and e represent 1 and $Ar^1$ and $Ar^5$ have the meanings given above, or from a compound of the formula

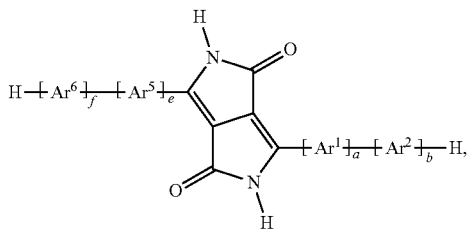
(XXXV)

wherein a and e represent 1, b and f represent 1, and $Ar^1$, $Ar^5$, $Ar^2$ and $Ar^6$ have the meanings given above.

Said starting compounds of the formulae

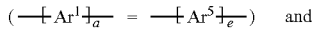 XXXIV

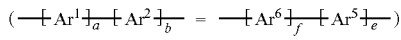 XXXV can be obtained as described in U.S. Pat. No. 4,579,949 by reacting (in the presence of a strong base) one mole of a disuccinate, like dimethyl succinate, with 1 mole of a nitrile of the formulae H—$Ar^1$—CN(XXXVI), or H—$Ar^6$—CN(XXXVII), or 1 mole of a nitrile of the formulae H—$Ar^2$—$Ar^1$—CN (XXXVIII), or H—$Ar^6$—$Ar^5$—CN (XXXIX).

Alternatively, said starting compounds of the formulae XXXIV and XXXV can be obtained as described in U.S. Pat. No. 4,659,775 by reacting a nitrile with a suitable ester, like a pyrrolinon-3-carboxylic ester derivative.

The thus obtained compound of the formula XXXIV or the thus obtained compound of the formula XXXV is then N-alkylated for introduction of the groups $R^1$ and $R^2$, e.g. by reaction with a bromide of the formula $R^1$—Br in the presence of a suitable base, like potassium carbonate, in a suitable solvent, like N-methyl-pyrrolidone. The reaction is carried out at a temperature from about room temperature to about 180° C., preferably from about 100° C. to about 170° C., e.g. at 140° C.

The thus obtained compound of the formula XL

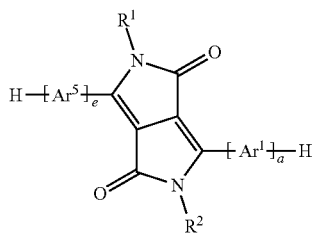
(XL)

wherein a and e represent 1, and $R^1$, $R^2$, $Ar^1$ and $Ar^5$ have the meanings given above, or the thus obtained compound of the formula XLI

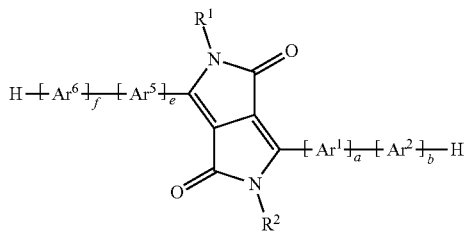
(XLI)

wherein a and e represent 1, b and f represent 1, and $R^1$, $R^2$, $Ar^2$ and $Ar^6$ have the meanings given above, is then reacted with a suitable brominating agent, like N-bromosuccinimide, to yield a compound of the formulae

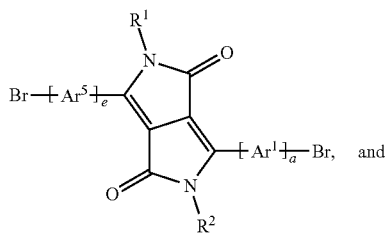
(XLII')

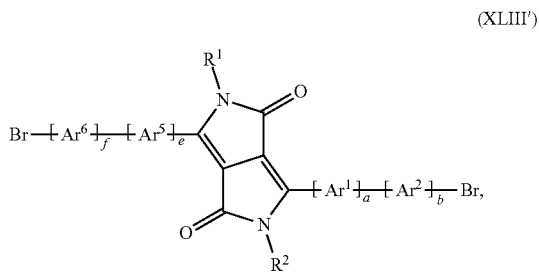
(XLIII')

respectively.

The bromination is carried out in a suitable solvent, like chloroform, using two equivalents of N-bromo-succinimide at a temperature between −30° C. and +50° C., preferably between −10° C. and room temperature, e.g. at 0° C.

The compounds of the formulae XLII' or XLIII' can then be "side-chain-elongated", by stepwise adding further groups $Ar^2$—H, $Ar^6$—H, $Ar^3$—$R^{13}$, and $Ar^7$—$R^{14}$. The step-wise addition of these groups can be effected e.g. by reacting a compound of the formulae XLII or XLIII with a suitable tin compound of the formula Ar—SnR$^{207}$R$^{208}$R$^{209}$, wherein Ar represents Ar$^2$—H, Ar$^6$—H, Ar$^3$—R$^{13}$, or Ar$^7$—R$^{14}$.

The reaction is carried out in the presence of a suitable palladium catalyst, like Pd(P[C$_6$H$_5$]$_3$)$_4$, in a suitable solvent, e.g. an aromatic hydrocarbon solvent, like toluene, at a temperature between about 50° C. and 180° C., e.g. under reflux, and under inert conditions including, inter alia, the use of dry solvents. After cooling down, the reaction mixture may be e.g. filtrated, e.g. on a double layer silica gel/Hyflo®, concentrated and the desired compound precipitated, e.g. by addition of methanol.

The "side-chain-elongation" of the compounds of the formulae XLII or XLIII with an additional thienyl residue can also be effected by Suzuki condensation, e.g. by reaction with a mixture of 2-thienylboronic acid pinacol ester, Pd$_2$(dba)$_3$ [tris(dibenzylideneacetone)-dipalladium)] and tri-tert-butyl-phosphonium-tetrafluoroborate in tetrahydrofurane.

The 2-thienylboronic acid pinacol ester may be obtained e.g. by adding substituted or un-substituted thiophene to a mixture prepared from n-butyl-lithium and diisopropylamine and by adding 2-isopropoxy-4,4,5,5-tetramethyl-1,3,2-dioxaborolane to the thus obtained mixture.

Analogously, the "side-chain-elongation" of the compounds of the formulae XLII or XLIII with an additional phenyl or biphenyl residue may be effected with phenyl-boronic acid pinacol ester or biphenyl-boronic acid pinacol ester.

Alternatively, for the manufacture of compounds of the formula I wherein the side chains of the formulae

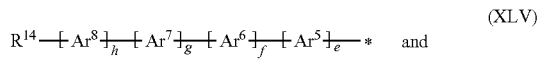

(XLV)

and

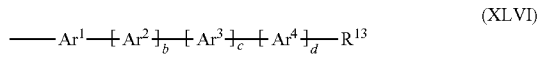

(XLVI)

are identical to each other and R$^{13}$ and R$^{14}$ are H, it is also possible to build up the complete side chains first and then reacting a nitrile of the formula

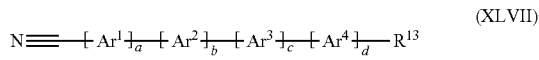

(XLVII)

with a suitable disuccinate, e.g. di-tert-amyl succinate. For example, a mixture of iron(III)chloride (FeCl$_3$), sodium, and tert-amylalcohol may be heated to 60-160° C., e.g. 110° C., before a mixture of the nitrile of the formula XLVII and di-tert-amyl succinate is added drop wise. After stirring the reaction mixture until the reaction is complete, e.g. for about 19 hours at 110° C., the reaction mixture is poured onto a water-methanol mixture.

Compounds of the formulae

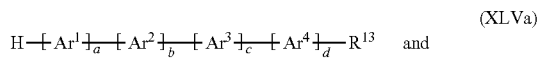

(XLVa)

and

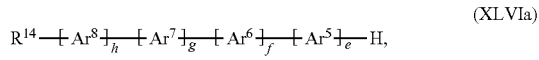

(XLVIa)

wherein R$^{13}$ and R$^{14}$ are H, containing the complete side chains can be manufactured e.g. by reacting a bromo derivative of the formula Br—Ar$^1$ etc. first with magnesium in diethyl ether and then adding the thus obtained Grignard solution to a solution in diethyl ether of Ni(dppp)Cl$_2$ and a mono- or, if desired, dibromo compound of the formula Br—Ar$^2$ or Br—Ar$^2$—Br, respectively, etc.

The conversion of a compound of the formula XLVIa into the nitrile of the formula XLVII may be effected e.g. by adding a solution of a compound of the formula XLVIa, e.g. in toluene, to the reaction mixture obtained by adding triflic anhydride to a solution of N-formylmethylaniline in e.g. toluene, and reacting the obtained aldehyde of the formula

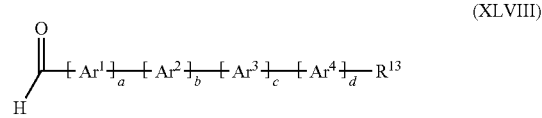

(XLVIII)

with hydroxylamine sulfate in e.g. dimethyl formamide.

The thus obtained compound of the formula I wherein R$^1$ and R$^2$ are hydrogen may then be transformed into a desired end product of the formula I wherein R$^1$ and R$^2$ are e.g. an aliphatic, cycloaliphatic, cycloaliphatic-aliphatic, or aromatic-aliphatic group, like especially such an hydrocarbon group, by N-alkylation, e.g. analogously as described above, or by heating a solution thereof and potassium carbonate in dimethyl formamide followed by addition of R$^1$—Br or R$^2$—Br, or by reaction with a suitable iodide of the formula R$^1$—I or R$^2$—I. For example, a mixture of a compound of the formula I wherein R$^1$ and R$^2$ are hydrogen in N-methyl-pyrrolidone is treated, preferably under cooling, e.g. to a temperature between about 0° C. and 10° C., e.g. about 5° C., with a suitable strong base, e.g. a suitable hydride, like an alkali metal hydride, e.g. sodium hydride. Thereafter, the iodide of the formula R$^1$—I or R$^2$—I is added. R$^1$ and R$^2$ are preferably identical.

Halogen is fluorine, chlorine, bromine and iodine.

C$_1$-C$_{25}$alkyl (C$_1$-C$_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethyl-pentyl, n-hexyl, 1-methylhexyl, 1,1,3,3,5,5-hexamethyl-hexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. C$_1$-C$_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. C$_1$-C$_4$alkyl is typically methyl, ethyl, n-propyl, isopropyl, n-butyl, sec.-butyl, isobutyl, tert.-butyl.

C$_2$-C$_{25}$alkenyl groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

C$_2$-C$_{25}$alkynyl is straight-chain or branched and preferably C$_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

An aliphatic hydrocarbon group having up to 25 carbon atoms is a linear or branched alkyl, alkenyl or alkynyl (also spelled alkinyl) group having up to 25 carbon atoms as exemplified above.

Alkylene is bivalent alkyl, i.e. alkyl having two (instead of one) free valencies, e.g. trimethylene or tetramethylene.

Alkenylene is bivalent alkenyl, i.e. alkenyl having two (instead of one) free valencies, e.g. —$CH_2$—CH=CH—$CH_2$—.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

A cycloaliphatic hydrocarbon group is a cycloalkyl or cycloalkenyl group which may be substituted by one or more aliphatic and/or cycloaliphatic hydrocarbon groups.

A cycloaliphatic-aliphatic group is an aliphatic group substituted by a cycloaliphatic group, wherein the terms "cycloaliphatic" and "aliphatic" have the meanings given herein and wherein the free valency extends from the aliphatic moiety. Hence, a cycloaliphatic-aliphatic group is for example a cycloalkyl-alkyl group.

A cycloalkyl-alkyl group is an alkyl group substituted by a cycloalkyl group, e.g. cyclohexyl-methyl.

A "cycloalkenyl group" means an unsaturated alicyclic hydrocarbon group containing one or more double bonds, such as cyclopentenyl, cyclopentadienyl, cyclohexenyl and the like, which may be unsubstituted or substituted by one or more aliphatic and/or cycloaliphatic hydrocarbon groups and/or condensed with phenyl groups.

For example, a cycloalkyl or cycloalkenyl group, in particular a cyclohexyl group, can be condensed one or two times with phenyl which can be substituted one to three times with $C_1$-$C_4$-alkyl. Examples of such condensed cyclohexyl groups are groups of the formulae:

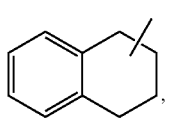 (XXIa)

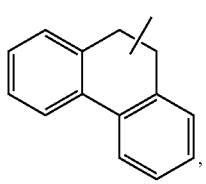 (XXIb)

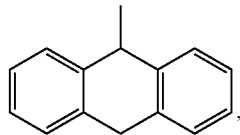 (XXII)

in particular

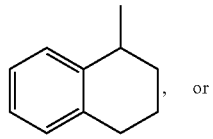 (XXIII)

or

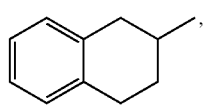 (XXIV)

which can be substituted in the phenyl moieties one to three times with $C_1$-$C_4$-alkyl.

A bivalent group of the formula XII wherein $R^{28}$ and $R^{27}$ together represent alkylene or alkenylene which may be both bonded via oxygen and/or sulfur to the thienyl residue and which may both have up to 25 carbon atoms, is e.g. a group of the formula

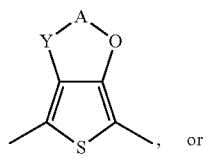 (XXIX)

or

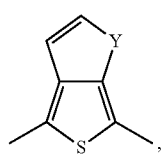 (XXX)

wherein A represents linear or branched alkylene having up to 25 carbon atoms, preferably ethylene or propylene which may be substituted by one or more alkyl groups, and Y represents oxygen or sulphur. For example, the bivalent group of the formula —Y-A-O— represents —O—$CH_2$—$CH_2$—O— or —O—$CH_2$—$CH_2$—$CH_2$—O—.

A group of the formula XI wherein two groups $R^{22}$ to $R^{26}$ which are in the neighborhood of each other, together represent alkylene or alkenylene having up to 8 carbon atoms, thereby forming a ring, is e.g. a group of the formula

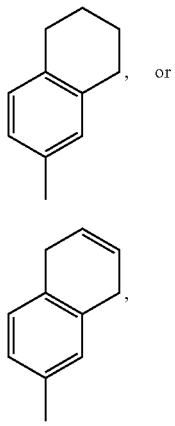

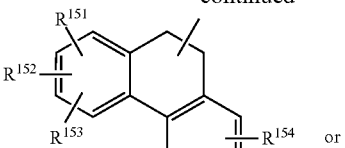

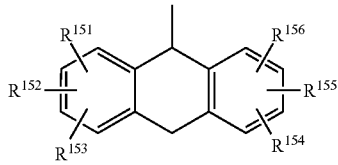

in particular

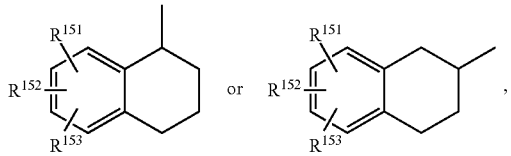

wherein $R^{151}$, $R^{152}$, $R^{153}$, $R^{154}$, $R^{155}$ and $R^{156}$ are independently of each other $C_1$-$C_8$-alkyl, $C_1$-$C_8$-alkoxy, halogen and cyano, in particular hydrogen.

$C_6$-$C_{24}$aryl ($C_6$-$C_{18}$aryl) is typically phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

$C_7$-$C_{25}$aralkyl is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

Heteroaryl is typically $C_2$-$C_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, (XXXII)

(XXXIII)

wherein in the group of the formula XXXII $R^{23}$ and $R^{24}$ together represent 1,4-butylene and in the group of the formula XXXIII $R^{23}$ and $R^{24}$ together represent 1,4-but-2-enylene.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The term "carbamoyl group" is typically a $C_{1-18}$carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

A cycloalkyl group is typically $C_5$-$C_{12}$cycloalkyl, such as, for example, cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

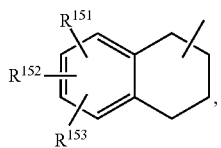

phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, a carbamoyl group, a nitro group or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

$C_1$-$C_{18}$alkyl interrupted by one or more O is, for example, $(CH_2CH_2O)_{1-9}$—$R^x$, where Rx is H or $C_1$-$C_{10}$alkyl, $CH_2$—$CH(OR^{y'})$—$CH_2$—O—$R^y$, where $R^y$ is $C_1$-$C_{18}$alkyl, and $R^{y'}$ embraces the same definitions as $R^y$ or is H.

If a substituent, such as, for example $R^3$, occurs more than one time in a group, it can be different in each occurrence.

The compounds of the formula I can show p-type transistor behavior and can be used as the semiconductor layer in semiconductor devices. Accordingly, the present invention also relates to a semiconductor device comprising as a semiconducting effective means a compound of the formula I.

The invention relates especially to a semiconductor device comprising as a semiconducting effective means a compound of the formula I described in the Examples selected from the compounds having the formulae A-1 to A-19, respectively, which are depicted in claim 10.

Preferably said semiconductor device is a diode, a photodiode, a sensor, an organic field effect transistor (OFET), a transistor for flexible displays, or a solar cell, or a device containing a diode and/or an organic field effect transistor, and/or a solar cell. There are numerous types of semiconductor devices. Common to all is the presence of one or more semiconductor materials. Semiconductor devices have been described, for example, by S. M. Sze in Physics of Semiconductor Devices, $2^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes in display applications or backlight in e.g. liquid crystal displays), photoconductors, current limiters, solar cells, thermistors, p-n junctions, field-effect diodes, Schottky diodes, and so forth. In each semiconductor device, the semiconductor material is combined with one or more metals and/or insulators to form the device. Semiconductor devices can be prepared or manufactured by known methods such as, for example, those described by Peter Van Zant in Microchip Fabrication, Fourth Edition, McGraw-Hill, New York (2000). In particular, organic electronic components can be manufactured as described by D. R. Gamota et al. in Printed Organic and Molecular Electronics, Kluver Academic Publ., Boston, 2004.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, $2^{nd}$ edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise silicon materials inclusive of various appropriate forms of silicon, inorganic glasses, ceramic foils, polymeric materials (for example, acrylics, polyester, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive oxides, such as indium tin oxide (ITO), or conducting inks/pastes comprised of carbon black/graphite or colloidal silver dispersions, optionally containing polymer binders can also be used. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material.

The gate dielectric (insulator) can be a material, such as, an oxide, nitride, or it can be a material selected from the family of ferroelectric insulators (e.g. organic materials such as poly(vinylidene fluoride/trifluoroethylene or poly(m-xylylene adipamide)), or it can be an organic polymeric insulator (e.g. poly(methacrylate)s, poly(acrylate)s, polyimides, benzocyclobutenes (BCBs), parylenes, polyvinylalcohol, polyvinylphenol (PVP), polystyrenes, polyester, polycarbonates) as for example described in J. Veres et al. Chem. Mat. 2004, 16, 4543 or A. Facchetti et al. Adv. Mat. 2005, 17, 1705. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulphide, including but not limited to $PbZr_xTi_{1-x}O_3$ (PZT), $Bi_4Ti_3O_{12}$, $BaMgF_4$, $Ba(Zr_{1-x}Ti_x)O_3$ (BZT). In addition, alloys, hybride materials (e.g. polysiloxanes or nanoparticle-filled polymers) combinations, and multilayers of these materials can be used for the gate dielectric. The thickness of the dielectric layer is, for example, from about 10 to 1000 nm, with a more specific thickness being about 100 to 500 nm, providing a capacitance in the range of 0.1-100 nanofarads (nF).

The source electrode and drain electrode are separated from the gate electrode by the gate dielectric, while the organic semiconductor layer can be over or under the source electrode and drain electrode. The source and drain electrodes can be any useful conductive material favourably providing a low resistance ohmic contact to the semiconductor layer. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or (ink jet) printing methods. The patterning of these electrodes can be accomplished by known methods such as shadow masking, additive photolithography, subtractive photolithography, printing, microcontact printing, and pattern coating.

The present invention further provides a thin film transistor device comprising a plurality of electrically conducting gate electrodes disposed on a substrate;

a gate insulator layer disposed on said electrically conducting gate electrodes;

a plurality of sets of electrically conductive source and drain electrodes disposed on said insulator layer such that each of said sets is in alignment with each of said gate electrodes;

an organic semiconductor layer disposed in the channel between source and drain electrodes on said insulator layer substantially overlapping said gate electrodes; wherein said organic semiconductor layer comprise a compound of the formula I.

An organic field effect transistor can have various designs. The most common design of a field-effect transistor is the Bottom-Gate Top-Contact (BGTC) design. Here, the gate is on top of the substrate and at the bottom of the dielectric layer, the semiconducting layer is at the top of the dielectric layer and the source/drain electrodes are on top of the semiconducting layer.

Another design of a field-effect transistor is the Top-Gate Bottom-Contact (TGBC) design. Here, the source/drain electrodes are on top of the substrate and at the bottom of the semiconducting layer, the dielectric layer is on top of the semiconducting layer and the gate electrode is on top of the dielectric layer.

The organic semiconductor layer is preferably formed by applying a solution and/or dispersion of a compound according to the present invention in an organic solvent to a suitable substrate and removing the solvent; or the organic semiconductor layer is formed by vacuum vapor deposition of a compound according to the present invention.

The present invention further provides a process for preparing a thin film transistor device comprising the steps of:

depositing a plurality of electrically conducting gate electrodes on a substrate;

depositing a gate insulator layer on said electrically conducting gate electrodes;

depositing a plurality of sets of electrically conductive source and drain electrodes on said layer such that each of said sets is in alignment with each of said gate electrodes;

depositing a layer comprising a compound of the formula I on said insulator layer such that said layer comprising the compound of formula I substantially overlaps said gate electrodes, thereby producing the thin film transistor device.

The above-mentioned layer comprising a compound of formula I may additionally comprise at least another material. The other material can be, but is not restricted to another compound of the formula I, a semi-conducting polymer, a polymeric binder, organic small molecules different from a compound of the formula I, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more small molecules of the formula I and a polymeric binder. The ratio of the small molecules of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA). With this technique, a degradation of the electrical performance can be avoided (cf. WO 2008/001123 A1).

Any suitable substrate can be used to prepare the thin films of the compounds of the formula I. Preferably, the substrate used to prepare the above thin films is a metal, silicon, plastic, paper, coated paper, fabric, glass or coated glass.

In a preferred embodiment, the deposition of at least one compound of the general formula I (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of the general formula I are suitable particularly advantageously for use in a PVD process, since they essentially do not decompose and/or form undesired by-products. The material deposited is obtained in high purity. In a specific embodiment, the deposited material is obtained in the form of crystals or comprises a high crystalline content. In general, for the PVD, at least one compound of the general formula I is heated to a temperature above its evaporation temperature and deposited on a substrate by cooling below the crystallization temperature. The temperature of the substrate in the deposition is preferably within a range from about 20 to 250° C., more preferably from 50 to 200° C.

The resulting semiconductor layers generally have a thickness which is sufficient for ohmic contact between source and drain electrodes. The deposition can be effected under an inert atmosphere, for example under nitrogen, argon or helium. The deposition is effected typically at ambient pressure or under reduced pressure. A suitable pressure range is from about $10^{-7}$ to 1.5 bar.

The compound of the formula I is preferably deposited on the substrate in a thickness of from 10 to 1000 nm, more preferably from 15 to 250 nm. In a specific embodiment, the compound of the formula I is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic SemiConductors", Journal of Crystal Growth 187 (1998), pages 449-454, and in "Physical Vapor Growth of Centimeter-sized Crystals of α-Hexathiophene", Journal of Crystal Growth 1982 (1997), pages 416-427, which are incorporated here by reference.

Alternatively, a TFT is fabricated, for example, by solution deposition of a compound of the formula I on a highly doped silicon substrate covered with a thermally grown oxide layer followed by vacuum deposition and patterning of source and drain electrodes.

In yet another approach, a TFT is fabricated by deposition of source and drain electrodes on a highly doped silicon substrate covered with a thermally grown oxide and then solution deposition of the compound of the formula I to form a thin film.

The gate electrode could also be a patterned metal gate electrode on a substrate or a conducting material such as a conducting polymer, which is then coated with an insulator applied either by solution coating or by vacuum deposition on the patterned gate electrodes.

Self-assembled monolayer (SAMs) interposed between a gate dielectric and an organic semiconductor layer have been utilised to create more compatible interfaces. Early examples of using SAMs included using a silazane or silane coupling agents on silicon oxide surfaces. Other approaches have been to include a polymeric interlayer between the dielectric and semiconductor layers; or alkyl phosphonic acid, or fluoro alkyl phosphonic acid SAMs (see, for example, U. Kraft et al., J. Mater. Chem. 20 (2010) 6416-18).

Any suitable solvent can be used to dissolve, and/or disperse a compound of the formula I, provided it is inert and can be removed partly, or completely from the substrate by conventional drying means (e.g. application of heat, reduced pressure, airflow etc.). Suitable organic solvents for processing the semiconductors of the invention include, but are not limited to, aromatic or aliphatic hydrocarbons, halogenated such as chlorinated or fluorinated hydrocarbons, esters, ethers amides, such as chloroform, tetrachloroethane, tetrahydrofuran, toluene, tetraline, anisole, xylene, ethyl acetate, methyl ethyl ketone, dimethyl form amide, dichlorobenzene, trichlorobenzene, propylene glycol monomethyl ether acetate (PG-MEA) and mixtures thereof. The solution, and/or dispersion is then applied by a method, such as, spin-coating, dip-coating, screen printing, microcontact printing, doctor blading or other solution application techniques known in the art on the substrate to obtain thin films of the semiconducting material.

The term "dispersion" covers any composition comprising a compound of the formula I, which is not fully dissolved in a solvent. The dispersion can be done selecting a composition including at least a compound of formula I, or a mixture containing a compound of formula I, and a solvent, wherein the polymer exhibits lower solubility in the solvent at room temperature but exhibits greater solubility in the solvent at an elevated temperature, wherein the composition gels when the elevated temperature is lowered to a first lower temperature without agitation;

dissolving at the elevated temperature at least a portion of the compound of the formula I in the solvent; lowering the temperature of the composition from the elevated temperature to the first lower temperature; agitating the composition to disrupt any gelling, wherein the agitating commences at any time prior to, simultaneous with, or subsequent to the lowering the elevated temperature of the composition to the first lower temperature; depositing a layer of the composition wherein the composition is at a second lower temperature lower than the elevated temperature; and drying at least partially the layer.

The dispersion can also be constituted of (a) a continuous phase comprising a solvent, a binder resin, and optionally a dispersing agent, and (b) a disperse phase comprising a compound of formula I, or a mixture containing a compound of formula I of the present invention. The degree of solubility of the compound of formula I in the solvent may vary for example from 0.5% to about 20% solubility, particularly from 1% to about 5% solubility.

Preferably, the thickness of the organic semiconductor layer is in the range of from about 5 to about 1000 nm, especially the thickness is in the range of from about 10 to about 100 nm.

The compounds of the formula I can be used alone or in combination as the organic semiconductor layer of the semiconductor device. The layer can be provided by any useful means, such as, for example, vapor deposition and printing techniques. The compounds of the formula I which are sufficiently soluble in organic solvents can be solution deposited and patterned (for example, by spin coating, dip coating, ink jet printing, gravure printing, flexo printing, offset printing, screen printing, microcontact (wave)-printing, drop or zone casting, or other known techniques).

The compounds of the formula I can be used in integrated circuits comprising a plurality of OTFTs, as well as in various electronic articles. Such articles include, for example, radiofrequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like. Due to its ambi-polarity the material can also be used in Organic Light Emitting Transistors (OLET).

In addition, the invention provides organic photovoltaic (PV) devices (solar cells) comprising a compound of the formula I.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula I. Preferably, the photoactive layer is made of a compound of the formula I, as an electron donor and an acceptor material, like a fullerene, particularly a functionalized fullerene PCBM, as an electron acceptor. As stated above, the photoactive layer may also contain a polymeric binder. The ratio of the small molecules of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another polymer of formula I or any semi-conducting polymer provided that the polymers retain acceptor-type and electron mobility characteristics, organic small molecules, carbon nanotubes, inorganic particles (quantum dots, quantum rods, quantum tripods, $TiO_2$, ZnO etc.).

For heterojunction solar cells (bulk heterojunction solar cells) the active layer comprises preferably a mixture of a compound of the formula I and a fullerene, such as [60] PCBM (=6,6-phenyl-$C_{61}$-butyric acid methyl ester), or [70] PCBM, in a weight ratio of 1:1 to 1:3. methanofullerene (phenyl-$C_{61}$-butyric-acid-methyl-ester ([60]PCBM), i.e. 1-[3-(methoxycarbonyl)propyl]-1-phenyl-[6.6]$C_{61}$-3'H-cyclopropa[1,9][5,6]fullerene-$C_{60}$-lh-3'-butanoic acid 3'-phenyl methyl ester, is an effective solution processable n-type organic semiconductor. It is blended with conjugated polymers with nano-particles such as $C_{60}$.

The electrodes are preferably composed of metals or "metal substitutes". Herein the term "metal" is used to embrace both materials composed of an elementally pure metal, e.g., Mg, and also metal alloys which are materials composed of two or more elementally pure metals, e.g., Mg and Ag together, denoted Mg:Ag. Here, the term "metal substitute" refers to a material that is not a metal within the normal definition, but which has the metal-like properties that are desired in certain appropriate applications. Commonly used metal substitutes for electrodes and charge transfer layers would include doped wide-bandgap semiconductors, for example, transparent conducting oxides such as indium tin oxide (ITO), gallium indium tin oxide (GITO), and zinc indium tin oxide (ZITO). Another suitable metal substitute is the transparent conductive polymer polyanaline (PANI) and its chemical relatives, or PEDOT:PSS. Metal substitutes may be further selected from a wide range of non-metallic materials, wherein the term "non-metallic" is meant to embrace a wide range of materials provided that the material is free of metal in its chemically uncombined form. Highly transparent, non-metallic, low resistance cathodes or highly efficient, low resistance metallic/non-metallic compound cathodes are, for example, disclosed in U.S. Pat. No. 6,420,031 and U.S. Pat. No. 5,703,436.

The substrate can be, for example, a plastic (flexible substrate), or glass substrate.

In another preferred embodiment of the invention, a smoothing layer is situated between the anode and the photoactive layer. A preferred material for this smoothing layer comprises a film of 3,4-polyethylenedioxythiophene (PEDOT), or 3,4-polyethylenedioxy-thiophene:polystyrene-sulfonate (PEDOT:PSS).

In a preferred embodiment of the present invention, the photovoltaic cell comprises, as described for example, in U.S. Pat. No. 6,933,436 a transparent glass carrier, onto which an electrode layer made of indium/tin oxide (ITO) is applied. This electrode layer generally has a comparatively rough surface structure, so that it is covered with a smoothing layer made of a polymer, typically PEDOT, which is made electrically conductive through doping. The photoactive layer is made of two components, has a layer thickness of, for example, 100 nm to a few μm depending on the application method, and is applied onto this smoothing layer. The photoactive layer is made of a compound of the formula I, as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

Before a counter electrode is applied, a thin transition layer, which must be electrically insulating, having a layer thickness of, for example, 0.6 nm, is applied to the photoactive layer. In this exemplary embodiment, this transition layer is made of an alkali halogenide, namely a lithium fluoride, which is vapor deposited in a vacuum of $2 \cdot 10^{-6}$ torr at a rate of 0.2 nm/minute.

If ITO is used as a hole-collecting electrode, aluminum, which is vapor deposited onto the electrically insulating transition layer, is used as an electron-collecting electrode. The electric insulation properties of the transition layer obviously prevent influences which hinder the crossing of the charge carrier from being effective, particularly in the transition region from the photoactive layer to the transition layer.

In a further embodiment of the invention, one or more of the layers may be treated with plasma prior to depositing the next layer. It is particularly advantageous that prior to the deposition of the PEDOT:PSS layer the anode material is subjected to a mild plasma treatment.

As an alternative to PEDOT:PSS a crosslinkable hole-transport material based on triarylamines as referenced in Macromol. Rapid Commun. 20, 224-228 (1999) can be used. In addition to the triarylamine material the layer can also include an electron acceptor to improve electron transport. Such compounds are disclosed in US 2004/0004433. Preferably, the electron acceptor material is soluble in one or more organic solvents. Typically, the electron acceptor material is present in the range of 0.5 to 20% by weight of the triarylamine material.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the compounds of the formula I can also be used alone or together with other materials in or as alignment layers in LCD or OLED devices, as described for example in US2003/0021913.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Materials and Methods 2,5-Di(2-ethylhexyl)-3,6-bis(5-bromo-thiophen-2-yl)pyrrolo[3,4-c]-pyrrole-1,4-dione 2 is prepared according to the literature (Tamayo, A. B.; Tantiwiwat, M.; Walker, B.; Nguyen, T.-Q. J. Phys. Chem. C 2008, 112, 15543-15552. (b) Huo, L.; Hou, J.; Chen, H.-Y.; Zhang, S.; Jiang, Y.; Chen, T. L.; Yang, Y. Macromolecules 2009, 42, 6564-6571).

All other reagents and solvents are obtained from commercial suppliers and purified and dried according to standard procedures (Perrin, D. D.; Armarego, W. L.; Perrin, D. R. Purification of Laboratory Chemicals—2nd ed.; Pergamon Press Ltd.: Oxford 1980). Column chromatography is performed on silica gel (Merck Silica 60, particle size 0.040-0.063 mm). Solvents for spectroscopic studies are of spectroscopic grade and used as received. Elemental analysis is performed on a CHNS 932 analyzer (Leco Instruments GmbH, Monchengladbach, Germany). $^1$H spectra are recorded in CD2Cl$_2$ on a Bruker Avance 400 spectrometer. Residual undeuterated solvent is used as internal standard (5.32 ppm for $^1$H). High-resolution ESI-TOF mass spectrometry is carried out on a microTOF focus instrument (Bruker Daltronik GmbH). UV/Vis measurements are performed in a conventional quartz cell (light pass 10 mm) on a Perkin-Elmer Lambda 950 spectrometer. For cyclic voltammetry, a standard commercial electrochemical analyzer (EC epsilon; BAS Instruments, UK) with a three electrode single-compartment cell is used. Dichloromethane (HPLC grade) is dried over calcium hydride under argon and degassed before using. The supporting electrolyte tetrabutylammonium hexafluorophosphate (TBAHFP) is prepared according to the literature (Fry, A. J. Laboratory Techniques in Electroanalytical Chemistry 2nd ed.; Marcel Dekker Ltd.: New York 1996), and recrystallized from ethanol/water. The measurements are carried out in dichloromethane at a concentration of about $10^{-4}$M with ferrocene (Fc) as internal standard for the calibration of the potential. Ag/AgCl reference electrode is used. A Pt disc and a Pt wire are used as working and auxiliary electrodes, respectively.

Example 1

2,5-Di(2-ethylhexyl)-3,6-bis(5-cyano-thiophen-2-yl)pyrrolo[3,4-c]-pyrrole-1,4-dione (A-1)

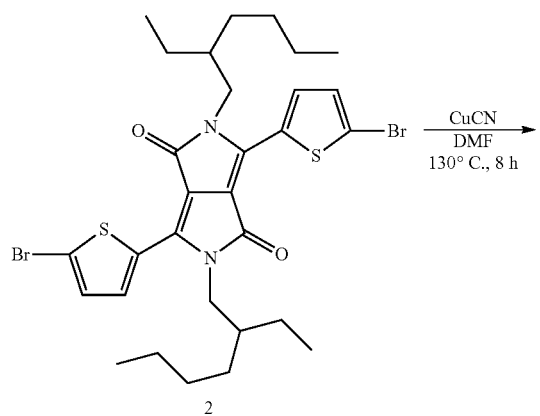

A mixture of compound 2 (249 mg, 0.365 mmol) and copper(I)cyanide (1.50 g, 16.7 mmol) in dry DMF (8 mL) is heated under argon for 8 h at 130° C. The reaction mixture is allowed to cool down to room temperature and a solution of sodium cyanide (180 g) in water (20 mL) is added. The aqueous phase is extracted with dichloromethane. The solvent is removed under reduced pressure and the residue is purified by column chromatography (dichloromethane) affording a dark violet solid (48.8 mg, 31%).

$^1$H NMR (400 MHz, CD$_2$Cl$_2$): δ=8.82 (d, $^3$J=4.2 Hz, 2H), 7.76 (d, $^3$J=4.2 Hz, 2H), 4.03-3.91 (m, 4H), 1.84-1.72 (m, 2H), 1.40-1.18 (m, 16H), 0.91-0.82 (m, 12H).

$^{13}$C NMR (101 MHz, CD$_2$Cl$_2$): δ=161.5, 139.8, 138.3, 135.7, 134.8, 113.9, 113.7, 110.9, 46.4, 39.7, 30.5, 28.7, 23.9, 23.4, 14.2, 10.5.

HRMS (ESI, acetonitrile/CHCl$_3$ 1:1, pos. mode): Calcd. for [M+H]C$_{32}$H$_{39}$N$_4$O$_2$S$_2$ 575.2510. Found 575.2510.

Elemental Anal. Calcd. for C$_{32}$H$_{38}$N$_4$O$_2$S$_2$: C, 66.87; H, 6.66; N, 9.75; S, 11.16; O, 3.94. Found: C, 66.60; H, 6.62; N, 9.77; S, 11.09.

CV (CH$_2$Cl$_2$, 0.1 M TBAHFP, vs. Fc/Fc$^+$): $E_{1/2}^{red}$ (X$^-$/X$^{2-}$)=−1.77 V, $E_{1/2}^{red}$ (X/X$^-$)=−1.24 V, $E_{1/2}^{ox}$ (X/X$^+$)=0.86 V.

UV-vis (CH$_2$Cl$_2$): $\lambda_{max}$ (∈)=586 (28500), 546 nm (26500 M$^{-1}$ cm$^{-1}$).

The redox behavior is studied by cyclic voltammetry in dichloromethane with ferrocene as internal standard showing two reversible reductions at −1.24 V and −1.77 V as well as one reversible oxidation at 0.86 V. The optical absorption in dichloromethane shows a maximum at 586 nm. The optical band gap is determined as 2.12 eV from the absorption maximum.

Application Example 1

To investigate the behavior of compound A-1 in an active layer of a field effect transistor, bottom-gate top-contact thin film transistors (TFT) with a 110 nm thick SiO$_2$/AlO$_x$/SAM gate dielectric are fabricated and measured in air. The organic compound is vacuum deposited at four different temperatures obtaining an optimum at 70° C. (Table 1). FIG. 1 shows the output and transfer characteristic of the TFT prepared under these conditions, leading to a hole mobility of 0.71 cm$^2$ V$^{-1}$ s$^{-1}$ determined in the saturation regime. In addition the device shows a high current on/off ratio (I$_{on}$/I$_{off}$) of 10$^6$.

TABLE 1

Summary of the performance for TFTs with compound A-1 fabricated at different deposition temperatures $T_D$.

| $T_D$/° C. | µ/cm² V⁻¹ s⁻¹ | $I_{on}/I_{off}$ | $U_T$/V |
|---|---|---|---|
| 20 | 0.2 | 10⁶ | −14 |
| 50 | 0.5 | 10⁶ | −19 |
| 70 | 0.7 | 10⁶ | −27 |
| 90 | 0.6 | 10⁶ | −25 |

The dependence of the mobility on the deposition temperature TD shows an increase of the mobility from 20° C. to 50° C. reaching a maximum at 70° C., whereas a slight decrease is obtained at 90° C. To correlate these observations with the morphology of the organic layer, the latter is investigated by atomic force microscopy (AFM). With increasing the deposition temperature, the organic compound forms larger grains and thus the number of crystalline domains decreases. A lower number of grain boundaries should be favorable for the charge transport and this leads to an increase of the field-effect mobility.

In summary, the novel type of efficient p-channel material, compound A-1, exhibits high hole-mobilities and on/off-ratios in vacuum deposited TFTs.

Example 2

2,5-Di-n-butyl-3,6-bis(5-cyano-thiophen-2-yl)pyrrolo[3,4-c]-pyrrole-1,4-dione (A-2)

The synthesis of 2,5-di-n-butyl-3,6-bis(5-bromo-thiophen-2-yl)pyrrolo[3,4-c]-pyrrole-1,4-dione is described in Zhou et al., Macromolecules 43 (2010) 821-826. 2,5-Di-n-butyl-3,6-bis(5-bromo-thiophen-2-yl)pyrrolo[3,4-c]-pyrrole-1,4-dione (1.08 g, 1.89 mmol) and copper(I)-cyanide (4.00 g, 44.6 mmol) in dry DMF (15 mL) are heated under argon at 130° C. for 315 min and at 165° C. for 40 min. The solvent is removed under reduced pressure and the crude product continuously extracted from the reaction mixture with chloroform. The extract is purified by column chromatography (dichloromethane) and washed with hexane affording 333 mg (38%) of a dark violet solid.

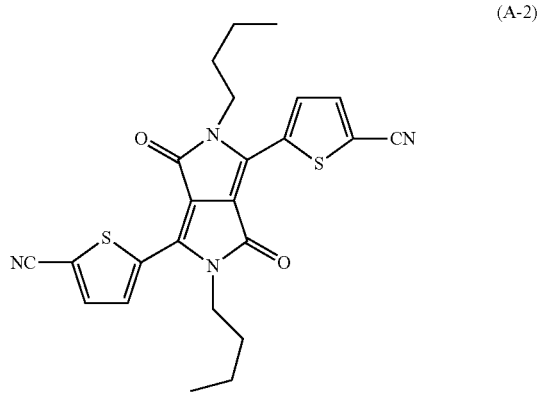 [SMILES: CCCCN1C(=O)C2=C(c3ccc(C#N)s3)N(CCCC)C(=O)C2=C1c1ccc(C#N)s1]

(A-2)

¹H NMR (400 MHz, CD₂Cl₂): δ 8.87 (d, ³J=4.2 Hz, 2H), 7.77 (d, ³J=4.2 Hz, 2H), 4.04 (t, ³J=7.6 Hz), 1.74-1.64 (m, 4H), 1.49-1.38 (m, 4H), 0.97 (t, ³J=7.4 Hz; 6H).

HRMS (ESI, pos-mode): calc. for [M−H]⁺ C₂₄H₂₃N₄O₂S₂: 463.1257. found: 463.1256.

Elemental analysis: calc. for C₂₄H₂₂N₄O₂S₂: C, 62.31; H, 4.79; N, 12.11; O, 6.92; S, 13.86. found: C, 62.32; H, 4.82; N, 12.05; S, 13.94.

Application Example 2

To investigate the behavior of compound A-2 in an active layer of a field effect transistor, bottom-gate top-contact thin film transistors (TFT) with a 110 nm thick SiO₂/AlO$_x$/SAM gate dielectric are fabricated and measured in air. The organic compound is vacuum deposited at three different temperatures (Table 2).

TABLE 2

Summary of the performance for TFTs with compound A-2 fabricated at different deposition temperatures $T_D$ on SiO₂/AlO$_x$/SAM with different self-assembled monolayers (SAMs).

| TD/° C. SAM | µ/cm² V⁻¹ s⁻¹ C₁₄H₂₉PO(OH)₂ | µ/cm² V⁻¹ s⁻¹ F₁₅C₁₈H₂₂PO(OH)₂ |
|---|---|---|
| 20 | 0.005 (p)-(n) | 0.01 (p)-(n) |
| 50 | 0.03 (p) | |
|    | 0.02 (n) | |
| 70 | 0.05 (p) | |
|    | 0.06 (n) | |

Example 3

2,5-Di-n-pentyl-3,6-bis(5-cyano-thiophen-2-yl)pyrrolo[3,4-c]-pyrrole-1,4-dione (A-17)

The synthesis of 2,5-di-n-pentyl-3,6-bis(5-bromo-thiophen-2-yl)pyrrolo[3,4-c]-pyrrole-1,4-dione is done in analogy to Zhou et al., Macromolecules 43 (2010) 821-826. 2,5-Di-n-pentyl-3,6-bis(5-bromo-thiophen-2-yl)pyrrolo[3,4-c]-pyrrole-1,4-dione (600 mg, 1.00 mmol) and copper(I)-cyanide (1.60 g, 18.0 mmol) in dry DMF (15 mL) are heated under argon at 120° C. for 60 min and at 165° C. for 80 min. The solvent is removed under reduced pressure and the crude product continuously extracted from the reaction mixture with chloroform. The extract is purified by column chromatography (dichloromethane) and washed with hexane affording 64.0 mg (13%) of a dark violet solid.

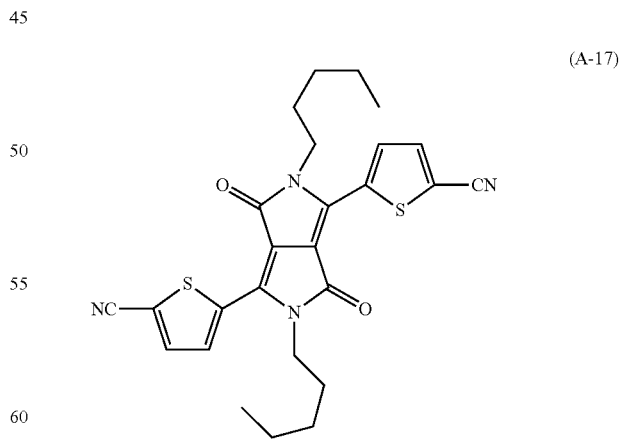

(A-17)

¹H NMR (400 MHz, CD₂Cl₂): δ 8.87 (d, ³J=4.2 Hz, 2H), 7.77 (d, ³J=4.2 Hz, 2H), 4.03 (t, ³J=7.8 Hz), 1.75-1.66 (m, 4H), 1.44-1.34 (m, 8H), 0.92 (t, ³J=7.1 Hz; 6H).

HRMS (ESI, pos-mode): calc. for [M+H] C₂₆H₂₇N₄O₂S₂: 491.1570. found: 491.1568.

Elemental analysis: calc. for $C_{26}H_{26}N_4O_2S_2$ C, 63.65; H, 5.34; N, 11.42; O, 6.52; S, 13.07. found C, 63.57; H, 5.23; N, 11.38; S, 13.05.

Application Example 3

To investigate the behavior of compound A-17 in an active layer of a field effect transistor, bottom-gate top-contact thin film transistors (TFT) with a 110 nm thick $SiO_2/AlO_x/SAM$ gate dielectric are fabricated and measured in air. The organic compound is vacuum deposited at two different temperatures (Table 3).

TABLE 3

Summary of the performance for TFTs with compound A-17 fabricated at different deposition temperatures $T_D$ on $SiO_2/AlO_x/SAM$ with different SAMs.

| $T_D$/° C. SAM | $\mu/cm^2 V^{-1} s^{-1}$ $C_{14}H_{29}PO(OH)_2$ | $\mu/cm^2 V^{-1} s^{-1}$ $F_{15}C_{18}H_{22}PO(OH)_2$ |
|---|---|---|
| 20 | 0.002 (n) | 0.025 (p)-(n) |
| 70 | 0.6 (p) | |
|    | 0.03 (n) | |

Example 4

2,5-Di-n-hexyl-3,6-bis(5-cyano-thiophen-2-yl)pyrrolo[3,4-c]-pyrrole-1,4-dione (A-3)

The synthesis of 2,5-di-n-hexyl-3,6-bis(5-bromo-thiophen-2-yl)pyrrolo[3,4-c]-pyrrole-1,4-dione is done in analogy to Zhou et al., Macromolecules 43 (2010) 821-826. 2,5-Di-n-hexyl-3,6-bis(5-bromo-thiophen-2-yl)pyrrolo[3,4-c]-pyrrole-1,4-dione (237 mg, 0.378 mmol) and copper(I)-cyanide (1.50 g, 17.0 mmol) are placed in a 25 mL-flask under argon. Dry DMF (10 mL) is added and the mixture is stirred at 130° C. for 4 h. The solvent is removed under reduced pressure and the residual solid is extracted with chloroform (250 mL). After removing the solvent the crude product is purified by column chromatography (dichloromethane). A violet solid is obtained (52 mg, 27%).

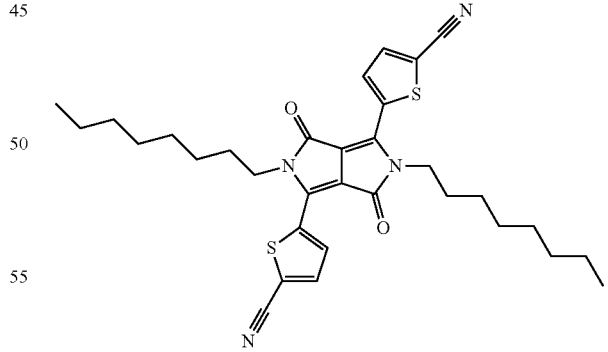

(A-3)

$^1$H-NMR (400 MHz in $CD_2Cl_2$): δ 8.86 (d, $^3J$=4.2 Hz, 2H), 7.77 (d, $^3J$=4.2 Hz, 2H), 4.03 (t, $^3J$=7.8 Hz, 4H), 1.75-1.65 (m, 4H), 1.46-1.27 (m, 12H), 0.90 (t, $^3J$=7.1 Hz, 6H).

HRMS (ESI, pos-mode): calc. for $C_{28}H_{30}N_4O_2S_2$ 518.1805. found 518.1807.

Application Example 4

To investigate the behavior of compound A-3 in an active layer of a field effect transistor, bottom-gate top-contact thin film transistors (TFT) with a 110 nm thick $SiO_2/AlO_x/SAM$ gate dielectric are fabricated and measured in air. The organic compound is vacuum deposited at 90° C. (Table 4).

TABLE 4

Summary of the performance for TFTs with compound A-3 fabricated on $SiO_2/AlO_x/SAM$ with different SAMs.

| $T_D$/° C. SAM | $\mu/cm^2 V^{-1} s^{-1}$ $C_{14}H_{29}PO(OH)_2$ | $\mu/cm^2 V^{-1} s^{-1}$ $F_{15}C_{18}H_{22}PO(OH)_2$ |
|---|---|---|
| 90 | $10^{-4}$ (p) | 0.06 (p) |
|    | 0.05 (n) | 0.03 (n) |

Example 5

2,5-Di-n-octyl-3,6-bis(5-cyano-thiophen-2-yl)pyrrolo[3,4-c]-pyrrole-1,4-dione (A-4)

The synthesis of 2,5-di-n-octyl-3,6-bis(5-bromo-thiophen-2-yl)pyrrolo[3,4-c]-pyrrole-1,4-dione is done in analogy to Zhou et al., Macromolecules 43 (2010) 821-826. 2,5-Di-n-octyl-3,6-bis(5-bromo-thiophen-2-yl)pyrrolo[3,4-c]-pyrrole-1,4-dione (483 mg, 0.708 mmol) and copper(I)-cyanide (1.40 g, 15.6 mmol) in dry DMF (10 mL) are heated under argon at 160° C. for 60 min. Then further 10 mL DMF are added and the mixture is stirred at 165° C. for 140 min. The solvent is removed under reduced pressure and the crude product continuously extracted from the reaction mixture with chloroform. The extract is purified by column chromatography (dichloromethane) and washed with hexane affording 96.5 mg (24%) of a dark violet solid.

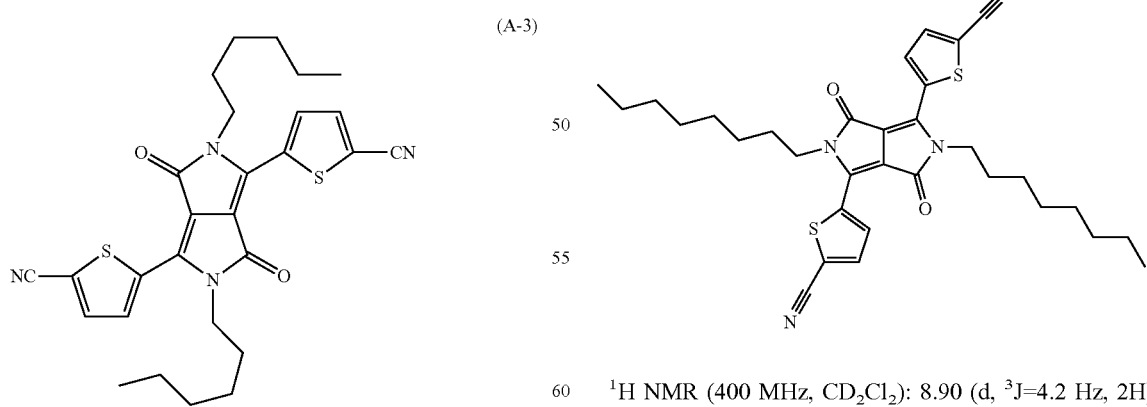

(A-4)

$^1$H NMR (400 MHz, $CD_2Cl_2$): 8.90 (d, $^3J$=4.2 Hz, 2H), 7.75 (d, $^3J$=4.2 Hz, 2H), 4.03 (t, $^3J$=7.8 Hz), 1.75-1.68 (m, 4H), 1.46-1.20 (m, 20H), 0.88 (t, $^3J$=6.9 Hz; 6H).

HRMS (ESI, acetonitrile/CHCl$_3$ 1:1, pos-mode): calc. for $C_{32}H_{39}N_4O_2S_2$ 575.2509. found: 575.2511.

Elemental analysis: calc. for C, 66.87; H, 6.66; N, 9.75; O, 5.57; S, 11.16. found: C, 66.67, H, 6.71, N 9.60, S 11.09.

Example 6

2,5-Bis(2-ethylhexyl)-3,6-bis(5'-dicarbonitrile-(2,2'-bithiophenyl-5-yl)-2,5-dihydro-pyrrolo[3,4-c]pyrrole-1,4-dione (A-18)

A degassed 3.1 mL H$_2$O solution of K$_3$PO$_4$ (947 mg, 4.47 mmol) is added to a degassed 27 mL THF solution of 2,5-bis(2-ethylhexyl)-3,6-bis[5-(4,4,5,5-tetramethyl-(1,3,2)dioxoborolan-2-yl)-thiophen-2-yl]-2,5-dihydro-pyrrolo[3,4-c]pyrrole-1,4-dione (1.14 g, 1.46 mmol), which can be synthesized in analogy to Example 37 of WO2009/047104, Pd$_2$(dba)$_3$ (39.0 mg, 0.04 mmol), P(t-Bu)$_3$×HBF$_4$ (23.0 mg, 0.08 mmol) and 2-bromo-thiophene-5-carbonitrile (1.1 g, 5.85 mmol) under argon atmosphere. After heating to 80° C. for 2 h, the solvent is removed under vacuum. Column chromatography (CH$_2$Cl$_2$) afforded 380 mg (0.51 mmol, 35%) of the product A-18 as a dark blue solid.

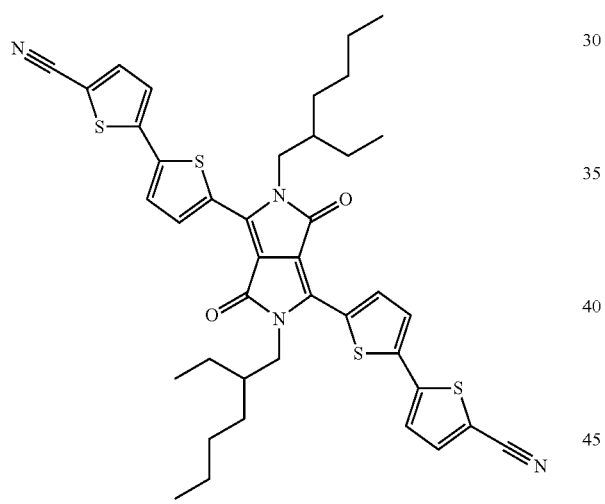

(A-18)

Mp 223-225° C.

$^1$H NMR (400 MHz, CD$_2$Cl$_2$): δ 8.90 (d, $^3$J=4.2 Hz, 2H), 7.60 (d, $^3$J=4.0 Hz, 2H), 7.46 (d, $^3$J=4.2 Hz, 2H), 7.31 (m, $^3$J=4.2 Hz, 2H), 4.02 (m, 4H), 1.87 (m, 2H), 1.32 (m, 16H), 0.89 (m, 12H).

$^{13}$C NMR (101 MHz, CD$_2$Cl$_2$): δ 162.0 (C), 143.5 (C), 140.1 (C), 139.9 (C), 136.8 (CH), 131.1 (C), 127.5 (CH), 125.4 (CH), 114.3 (C), 109.9 (C), 109.7 (C), 46.5 (CH$_2$), 39.9 (CH), 30.9 (CH$_2$), 29.1 (CH$_2$), 24.3 (CH$_2$), 23.7 (CH$_2$), 14.4 (CH$_3$), 10.9 (CH$_3$).

HRMS (ESI): m/z calcd. for C$_{40}$H$_{43}$N$_4$O$_2$S$_4$ [M+H]$^+$ 739.2269. found 739.2261.

Elemental analysis (%) calcd. for C$_{40}$H$_{42}$N$_4$O$_2$S$_4$: C, 65.01; H, 5.73; N, 7.58; S, 17.35. found: C, 65.03; H, 5.76; N, 7.41; S, 17.39. UV/vis (CH$_2$Cl$_2$): λ$_{max}$/nm (∈$_{max}$/m$^{-1}$ cm$^{-1}$) 586 (46600).

Example 7

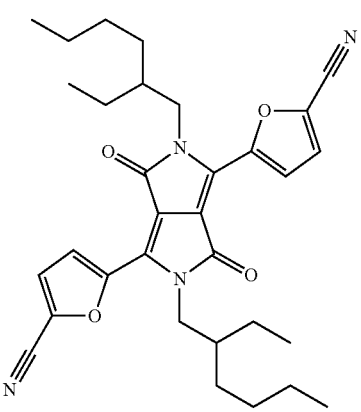

A-11

The compound of formula A-11 is synthesized in analogy to example 1, starting from [1254943-39-9] (Synthesis described in JACS 2010 132(44) 15547). Mass spectrum (APCI, negative mode): 543.3.

Example 8

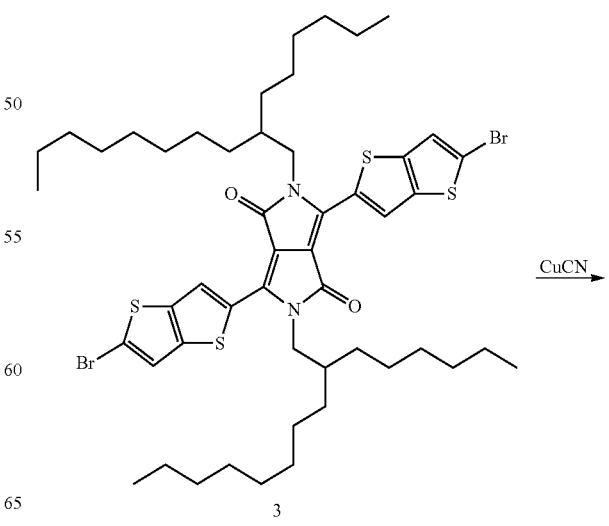

3

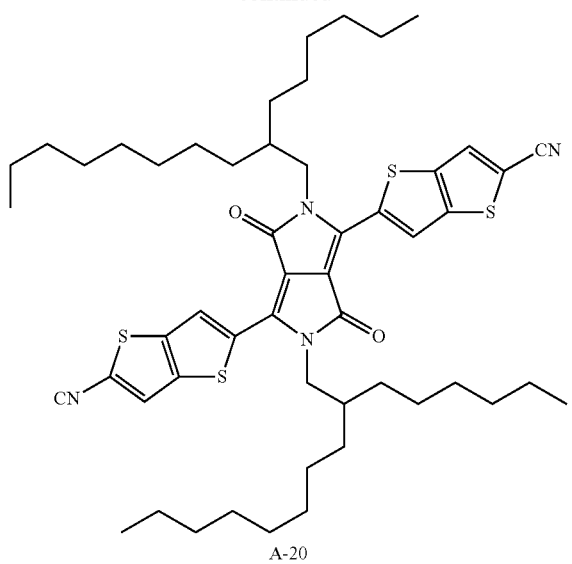

A-20

The compound of formula A-20 is synthesized in analogy to example 1, starting from compound 3 (the synthesis of compound 3 is done in analogy to example 1 of WO2010108873). Mass spectrum (APCI, positive mode): 911.13.

The invention claimed is:

1. A compound of formula

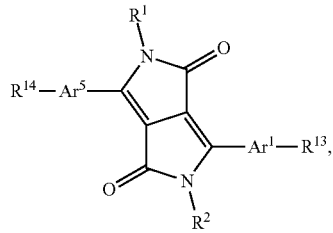
(Ia)

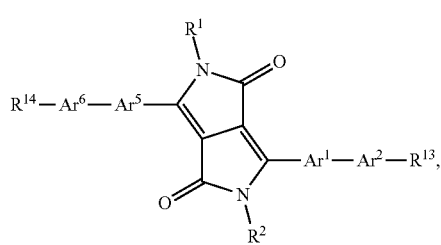
(Ib)

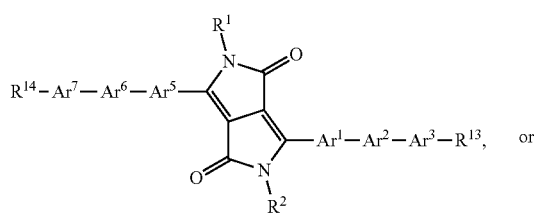
(Ic)

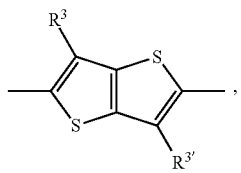
(Id)

wherein $R^1$ and $R^2$ are selected from the group consisting of a $C_1$-$C_{38}$alkyl group; a $C_1$-$C_{38}$alkyl group which is substituted by one or more halogen atoms; a $C_7$-$C_{25}$arylalkyl group, which can be substituted one to five times with $C_1$-$C_8$alkyl, $C_1$-$C_8$alkoxy and/or F; and pentafluorophenyl;

$R^{13}$ and $R^{14}$ are CN; and $Ar^1, Ar^2, Ar^3, Ar^4, Ar^5, Ar^6, Ar^7$ and $Ar^8$ are independently of each other

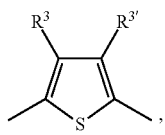
(Xa)

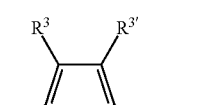
(Xm)

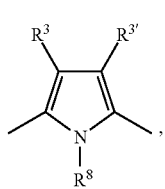
(Xn)

(Xo)

wherein $R^3$ and $R^{3'}$ are independently of each other hydrogen, halogen, $CF_3$, CN, $C_1$-$C_{25}$alkyl or $C_1$-$C_{25}$alkoxy, and $R^8$ is hydrogen or $C_1$-$C_{25}$alkyl.

2. The compound according to claim 1, wherein $Ar^1$ and $Ar^5$ are independently of each other

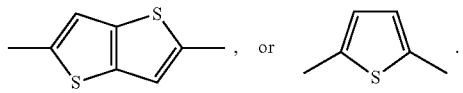

3. The compound according to claim 1, wherein $Ar^2$, $Ar^3$, $Ar^4$, $Ar^6$, $Ar^7$ and $Ar^8$ are independently of each other
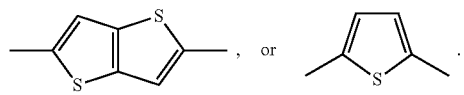
4. The compound according to claim 1, which is a compound of the formula
(IIIa)
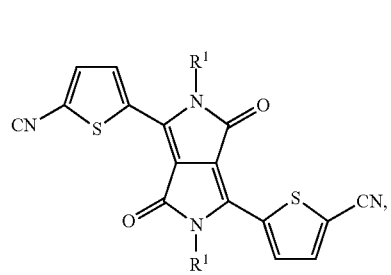
(IIIb)
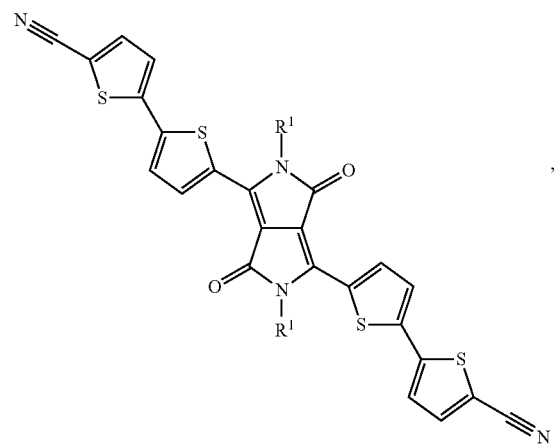
(IIIc)
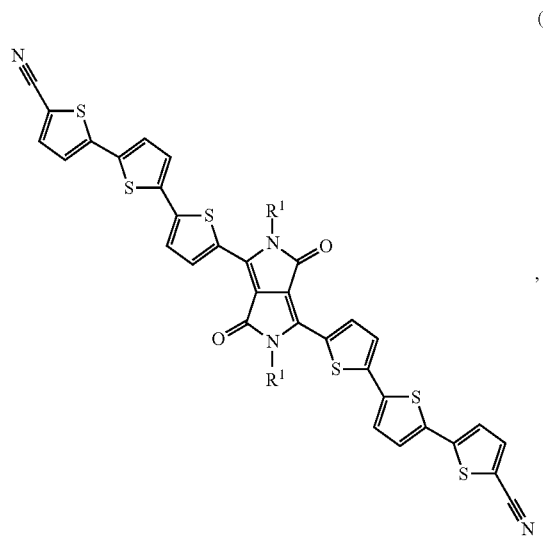
(IIId)
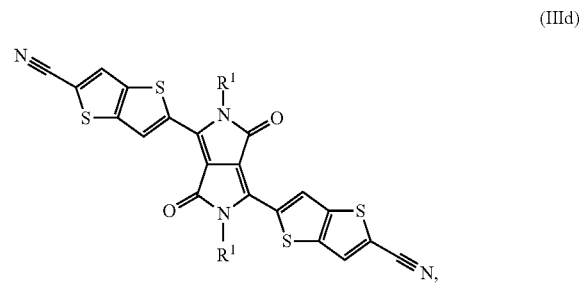

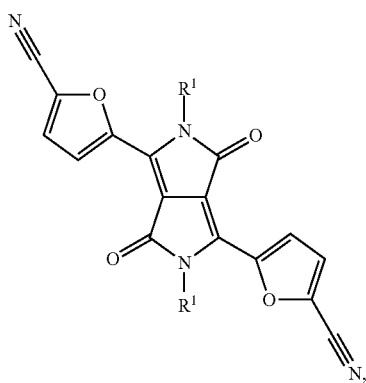
(IIIe)
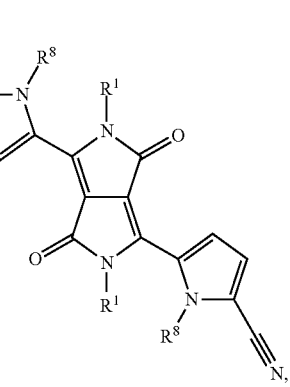
(IIIf)
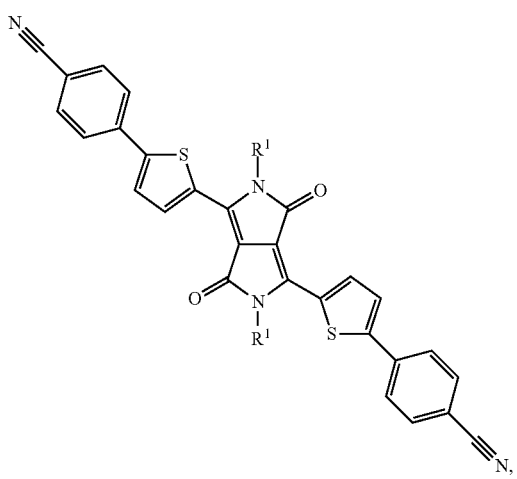
(IIIg)
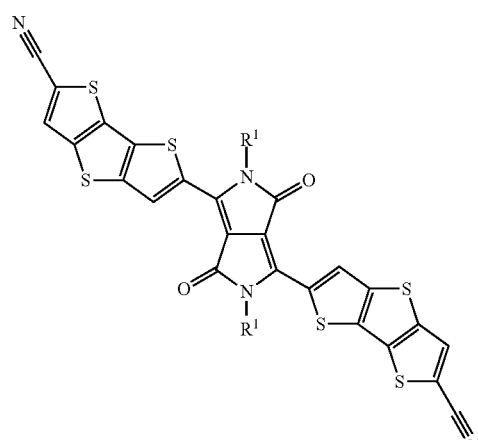
(IIIh)
, or
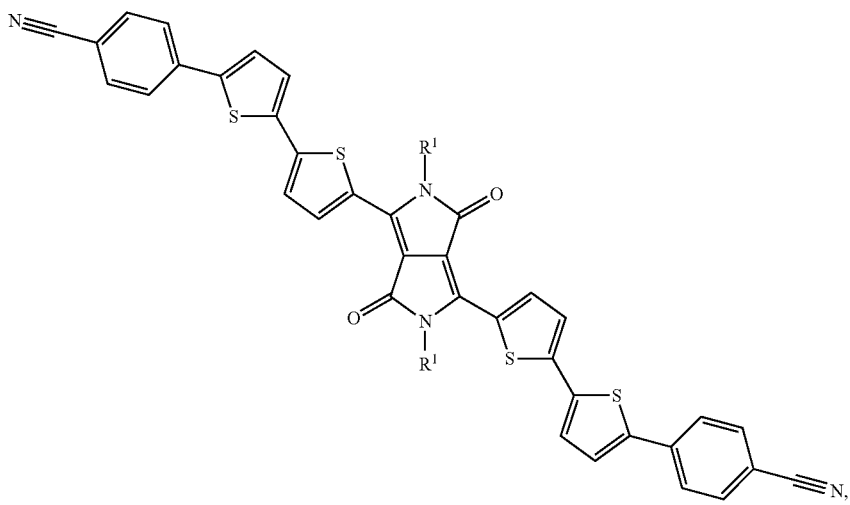
(IIIi)
wherein R¹ is a $C_1$-$C_{38}$alkyl group, a F containing $C_2$-$C_{36}$alkyl group, or
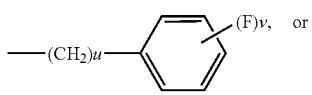 , or
-continued
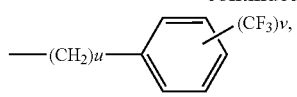
wherein u is 1, or 2, v is 1 to 5, and
R⁸ is hydrogen or $C_1$-$C_{25}$alkyl.

5. The compound according to claim 1, which is
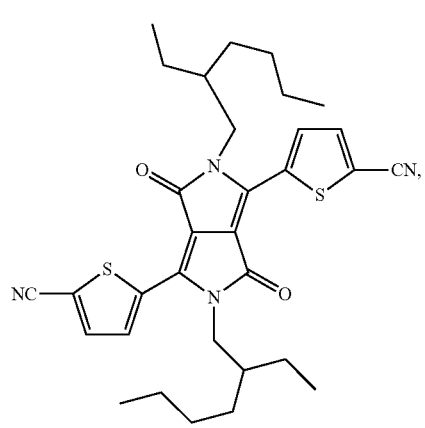 (A-1)
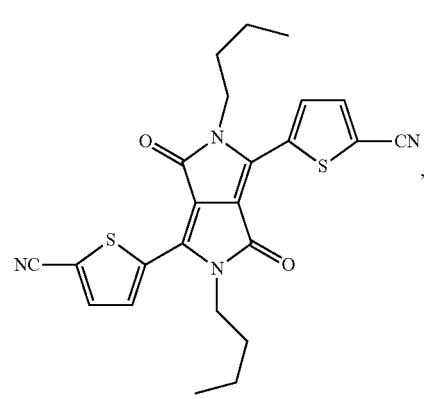 (A-2)
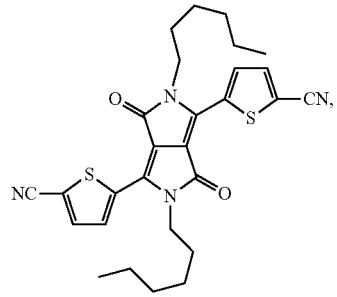 (A-3)
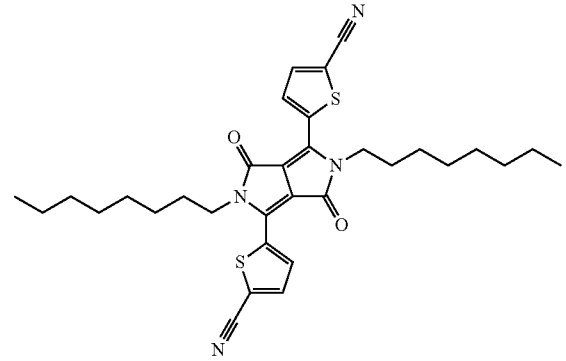 (A-4)
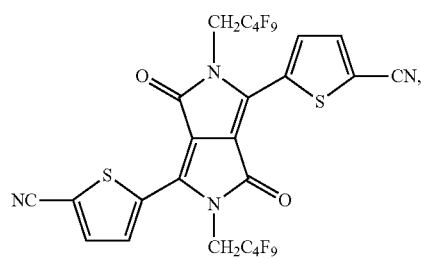 (A-5)
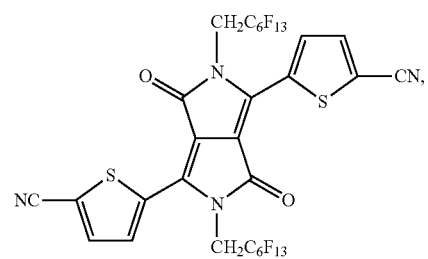 (A-6)

-continued
(A-7)
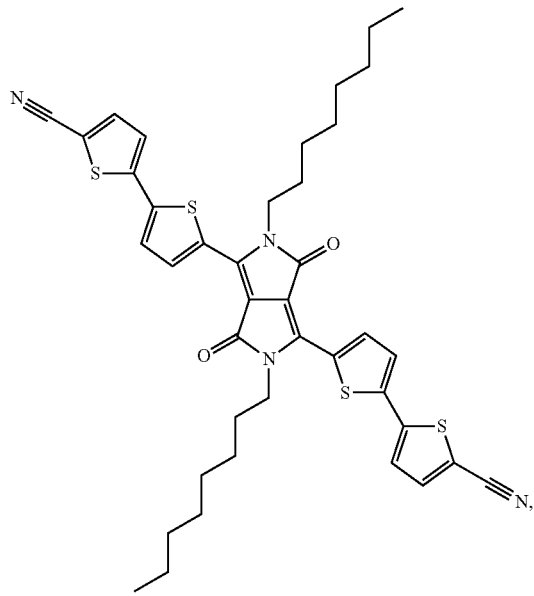
(A-8)
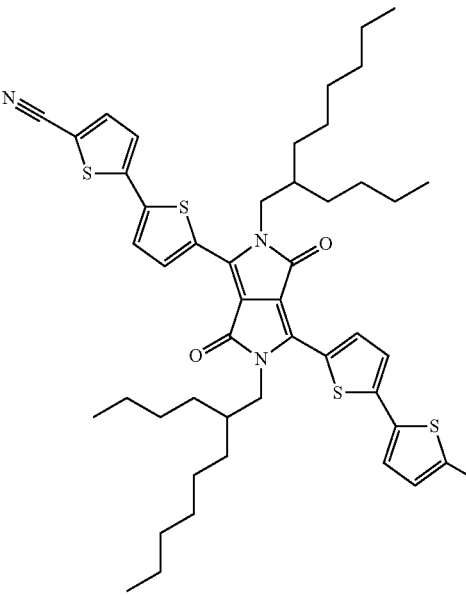
(A-9)
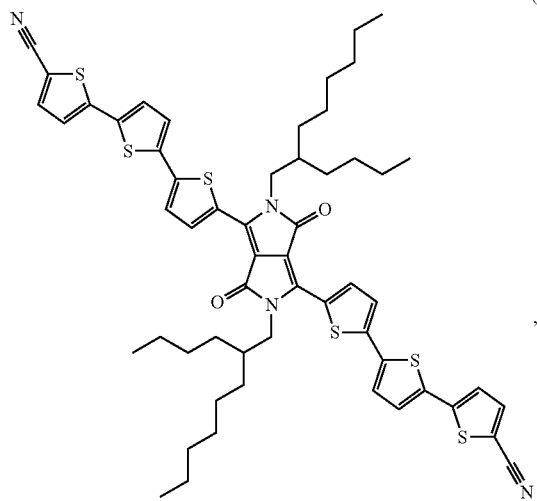
(A-10)
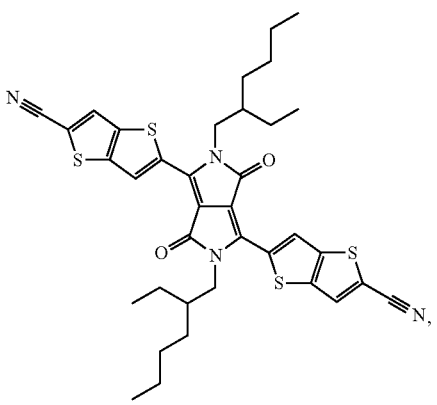
(A-11)
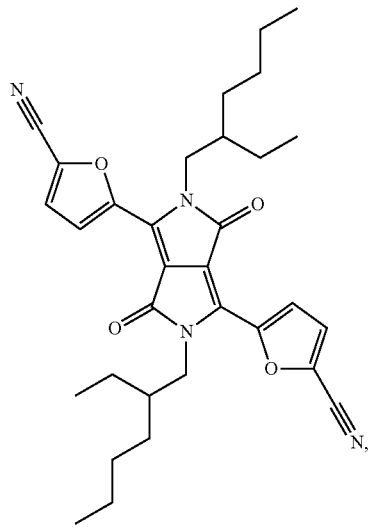
(A-12)
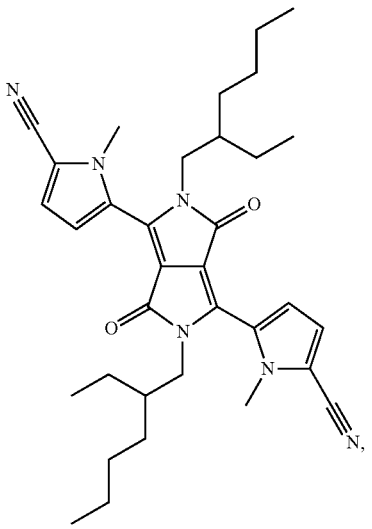

-continued
(A-13)
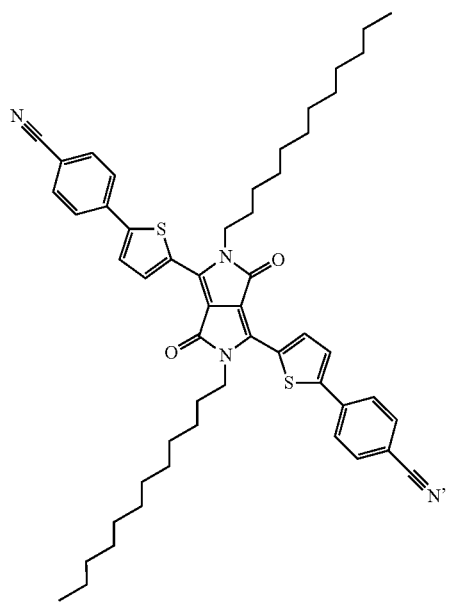
(A-14)
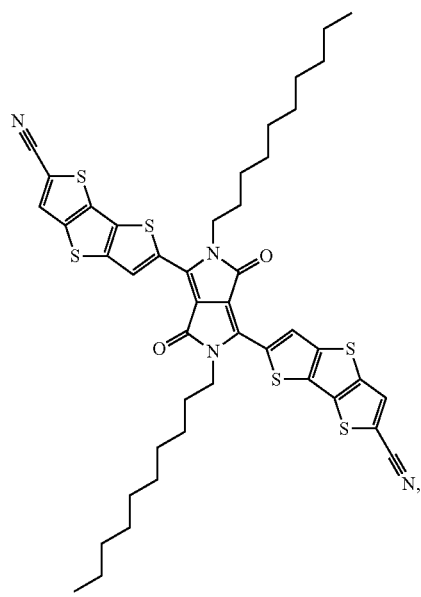
(A-15)
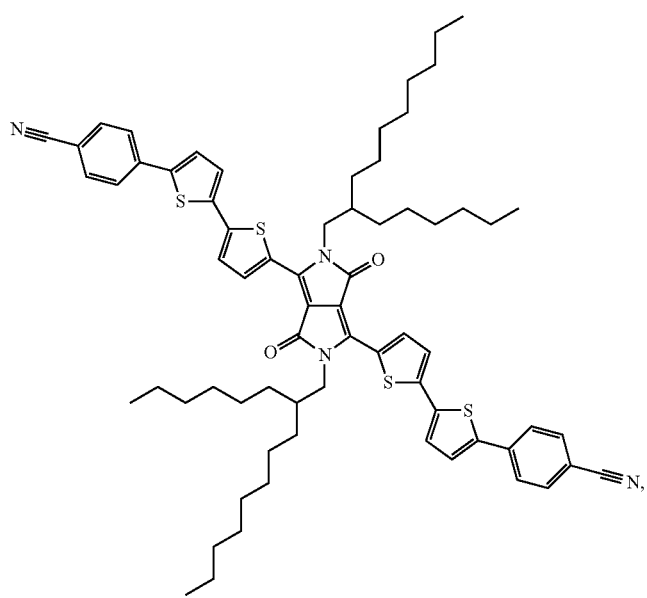
(A-16)
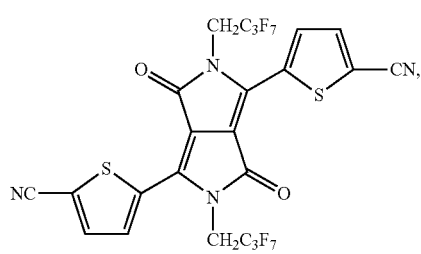
(A-17) or
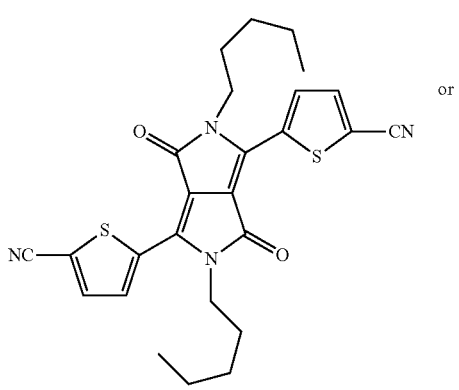

(A-19)

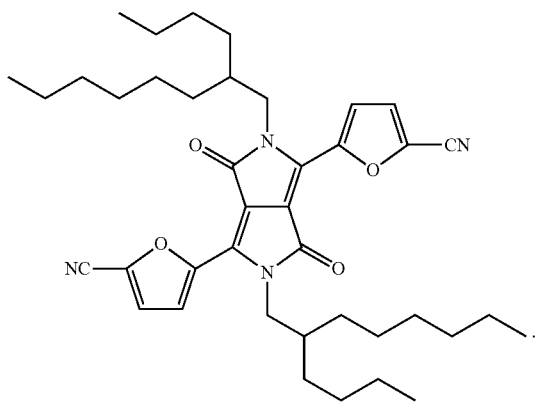

6. An organic semiconductor material, layer or component, comprising the compound according to claim 1.

7. A semiconductor device comprising as a semiconducting component a compound according to claim 1.

8. The semiconductor device according to claim 7 in the form of a diode, a photodiode, a sensor, an organic field effect transistor, a transistor for flexible displays, a RFID, or a (heterojunction) solar cell.

9. A process for the preparation of an organic semiconductor device, comprising: applying a solution and/or dispersion of a compound according to claim 1 in an organic solvent to a suitable substrate and removing the solvent.

10. A process for the preparation of the compound of claim 1, comprising reacting a precursor having a formula (Ia), (Ib), (Ic) or (Id) wherein $R^{13}$ and $R^{14}$ are each independently Cl, Br or I, with copper(I) cyanide.

11. A process for the preparation of an organic semiconductor device, comprising: depositing by vacuum vapor deposition a compound according to claim 1 on a substrate.

12. A semiconductor device comprising as a semiconducting component an organic semiconductor material, layer or component according to claim 6.

13. The compound according to claim 1, wherein $R^3$ and $R^{3'}$ are each independently a $CF_3$ group or a $C_3$-$C_{25}$ alkyl group.

14. The compound according to claim 1, wherein $R^8$ is a $C_3$-$C_{25}$alkyl group.

15. The compound according to claim 1, wherein $R^8$ is hydrogen.

16. The compound according to claim 1, wherein $R^1$ and $R^2$ are each independently a F containing $C_2$-$C_{36}$alkyl group.

17. The compound according to claim 1, wherein $R^1$ and $R^2$ are each independently a $CH_2C_nF_{2n+1}$ group wherein n is an integer of 1 to 10.

18. The compound according to claim 1, wherein $R^1$ and $R^2$ are each independently

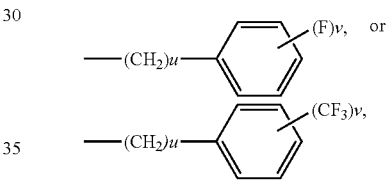

where u is 1, or 2, v is 1 to 5.

19. The compound according to claim 4, wherein $R^1$ is a $C_2$-$C_{12}$alkyl group or $CH_2C_nF_{2n+1}$ wherein n is an integer of 1 to 10.

20. The compound of claim 1, having the formula (Ia).
21. The compound of claim 1, having the formula (Ib).
22. The compound of claim 1, having the formula (Ic).
23. The compound of claim 1, having the formula (Id).

* * * * *